US009964869B2

(12) United States Patent
Okawa et al.

(10) Patent No.: US 9,964,869 B2
(45) Date of Patent: May 8, 2018

(54) TRIARYLAMINE DERIVATIVE, ELECTROPHOTOGRAPHIC PHOTOSENSITIVE MEMBER, AND METHOD FOR PRODUCING ELECTROPHOTOGRAPHIC PHOTOSENSITIVE MEMBER

(71) Applicant: KYOCERA Document Solutions Inc., Osaka (JP)

(72) Inventors: Kensuke Okawa, Osaka (JP); Hideki Okada, Osaka (JP); Jun Azuma, Osaka (JP); Fumio Sugai, Osaka (JP); Kensuke Kojima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days. days.

(21) Appl. No.: 15/345,726

(22) Filed: Nov. 8, 2016

(65) Prior Publication Data

US 2017/0131647 A1    May 11, 2017

(30) Foreign Application Priority Data

Nov. 9, 2015 (JP) ................... 2015-219403
Nov. 9, 2015 (JP) ................... 2015-219404

(51) Int. Cl.
*G03G 5/047* (2006.01)
*G03G 5/06* (2006.01)
(Continued)

(52) U.S. Cl.
CPC .......... *G03G 5/0612* (2013.01); *C07C 211/54* (2013.01); *C07C 217/92* (2013.01);
(Continued)

(58) Field of Classification Search
CPC ... C07C 211/54; C07C 217/92; G03G 5/0614; G03G 5/056
See application file for complete search history.

(56) References Cited

U.S. PATENT DOCUMENTS

2015/0261106 A1* 9/2015 Azuma ................ G03G 5/0614
430/58.8

FOREIGN PATENT DOCUMENTS

JP       2006-008670 A     12/2006
JP       2008-133221    *   6/2008  ............... G03G 5/06
(Continued)

OTHER PUBLICATIONS

Translation of JP 2010-026378 published Feb. 2010.*
(Continued)

*Primary Examiner* — Peter L Vajda
(74) *Attorney, Agent, or Firm* — Studebaker & Brackett PC

(57) ABSTRACT

A triarylamine derivative represented by general formula (1) below. In the general formula (1), $R_1$, $R_2$, $R_4$, $R_5$, $R_6$, $R_7$, $R_8$, and $R_9$ each represent, independently from one another, a hydrogen atom, an optionally substitute alkyl group having a carbon number of at least 1 and no greater than 6, an optionally substituted alkoxy group having a carbon number of at least 1 and no greater than 6, or an optionally substituted aryl group having a carbon number of at least 6 and no greater than 14, $R_3$ represents an alkyl group having a carbon number of at least 1 and no greater than 4, X represents an alkylene group having a carbon number of at least 1 and no greater than 6 or an oxygen atom, and n represents an integer of 1 to 3.

(Continued)

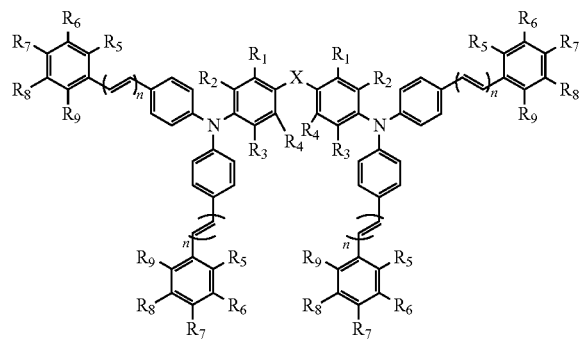

(1)

11 Claims, 3 Drawing Sheets

(51) Int. Cl.
  *C07C 211/54* (2006.01)
  *C07C 217/92* (2006.01)
  *G03G 5/05* (2006.01)

(52) U.S. Cl.
  CPC ......... *G03G 5/0525* (2013.01); *G03G 5/0567* (2013.01); *G03G 5/0609* (2013.01); *G03G 5/0614* (2013.01); *G03G 5/0618* (2013.01); *G03G 5/0672* (2013.01); *G03G 5/0696* (2013.01)

(56) References Cited

FOREIGN PATENT DOCUMENTS

JP  2008-133221 A  6/2008
JP  2010-026378  *  2/2010  ............. G03G 5/147

OTHER PUBLICATIONS

Translation of JP 2008-133221 published Jun. 2008.*
The extended European search report issued by the European Patent Office dated Mar. 17, 2017, which corresponds to European Patent Application No. 16197532.1-1451 and is related to U.S. Appl. No. 15/345,726.

* cited by examiner

TRIARYLAMINE DERIVATIVE, ELECTROPHOTOGRAPHIC PHOTOSENSITIVE MEMBER, AND METHOD FOR PRODUCING ELECTROPHOTOGRAPHIC PHOTOSENSITIVE MEMBER

INCORPORATION BY REFERENCE

The present application claims priority under 35 U.S.C. § 119 to Japanese Patent Applications No. 2015-219404, filed Nov. 9, 2015 and No. 2015-219403, filed Nov. 9, 2015. The contents of these applications are incorporated herein by reference in their entirety.

BACKGROUND

The present disclosure relates to a triarylamine derivative, an electrophotographic photosensitive member, and a method for producing an electrophotographic photosensitive member.

An electrophotographic photosensitive member is used in an electrophotographic image forming apparatus. The electrophotographic photosensitive member includes a photosensitive layer. For example, a multi-layer type electrophotographic photosensitive member or a single-layer type electrophotographic photosensitive member is used as the electrophotographic photosensitive member. The multi-layer type electrophotographic photosensitive member includes, as photosensitive layers, a charge generating layer having a charge generation function; and a charge transport layer having a charge transport function. The single-layer type electrophotographic photosensitive member includes, as a photosensitive layer, a single-layer type photosensitive layer having a charge generation function and a charge transport function. The photosensitive layer contains, for example, a compound represented by Formula (H-A) or (H-B) below.

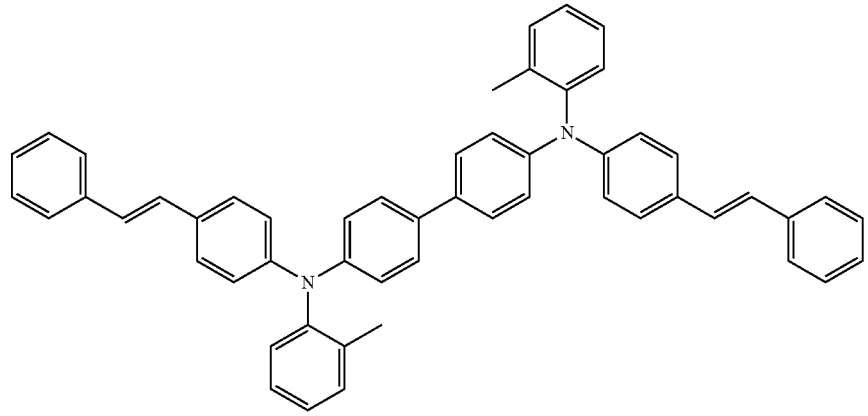

(H-A)

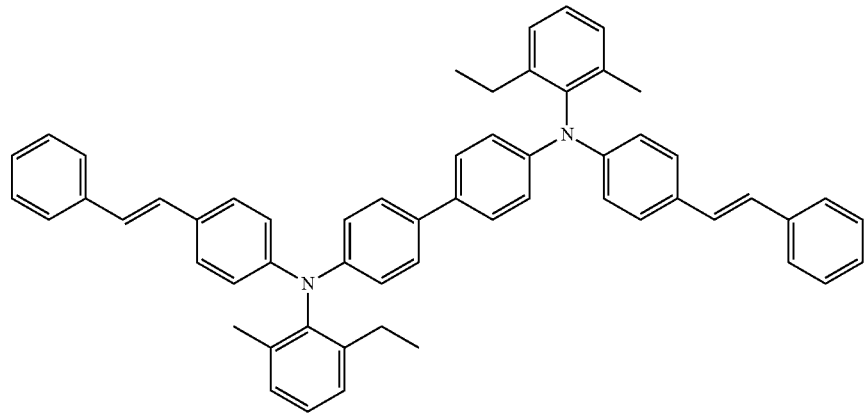

(H-B)

SUMMARY

A triarylamine derivative of the present disclosure is represented by general formula (1) below.

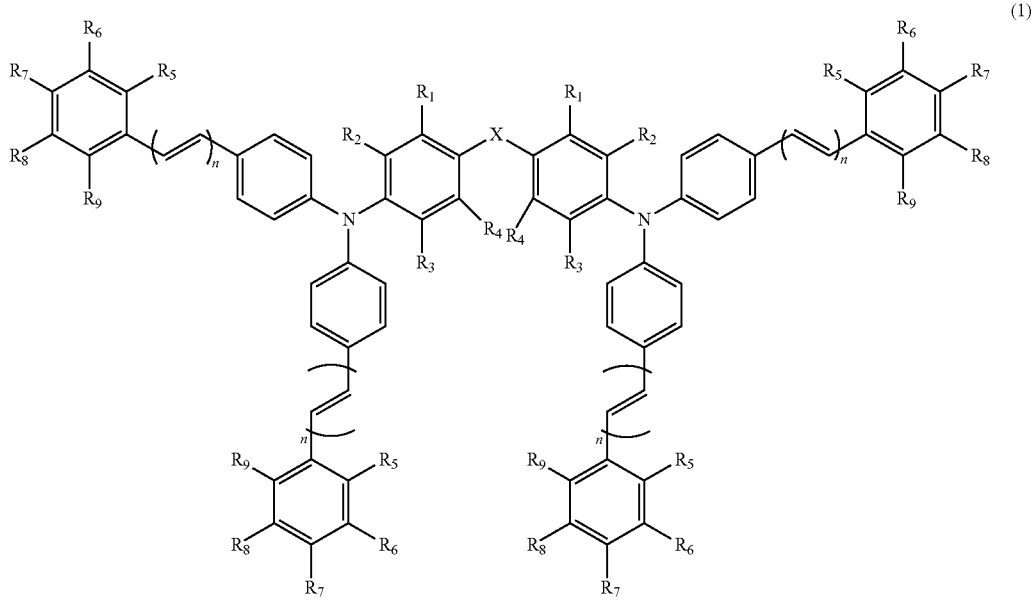

In the general formula (1), $R_1$, $R_2$, $R_4$, $R_5$, $R_6$, $R_7$, $R_8$, and $R_9$ each represent, independently from one another, a hydrogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 14. In the general formula (1), $R_3$ represents an alkyl group having a carbon number of at least 1 and no greater than 4. In the general formula (1), X represents an alkylene group having a carbon number of at least 1 and no greater than 6 or an oxygen atom. Symbol n represents an integer of at least 1 and no greater than 3.

The electrophotographic photosensitive member of the present disclosure includes: a conductive substrate; and a photosensitive layer containing a charge generating material and a hole transport material. The hole transport material is the triarylamine derivative described above.

A method for producing an electrophotographic photosensitive member of the present disclosure includes applying, onto the charge generating layer, an application liquid for charge transport layer formation containing at least a hole transport material, a binder resin, and a solvent; and removing at least part of the solvent to form a charge transport layer. The solvent contains at least one type of toluene, 1,4-dioxane, tetrahydrofuran, and o-xylene. The binder resin is a polycarbonate resin having a repeating unit represented by general formula (2) below. The hole transport material is the triarylamine derivative described above.

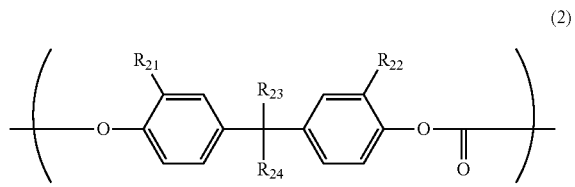

In the general formula (2), $R_{21}$ and $R_{22}$ each represent, independently from each other, a hydrogen atom, an alkyl group, or an aryl group, and $R_{23}$ and $R_{24}$ each represent, independently from each other, a hydrogen atom, an alkyl group, or an aryl group, or $R_{23}$ and $R_{24}$ bond to each other to represent a cycloalkylidene group.

DETAILED DESCRIPTION

Figure 1:
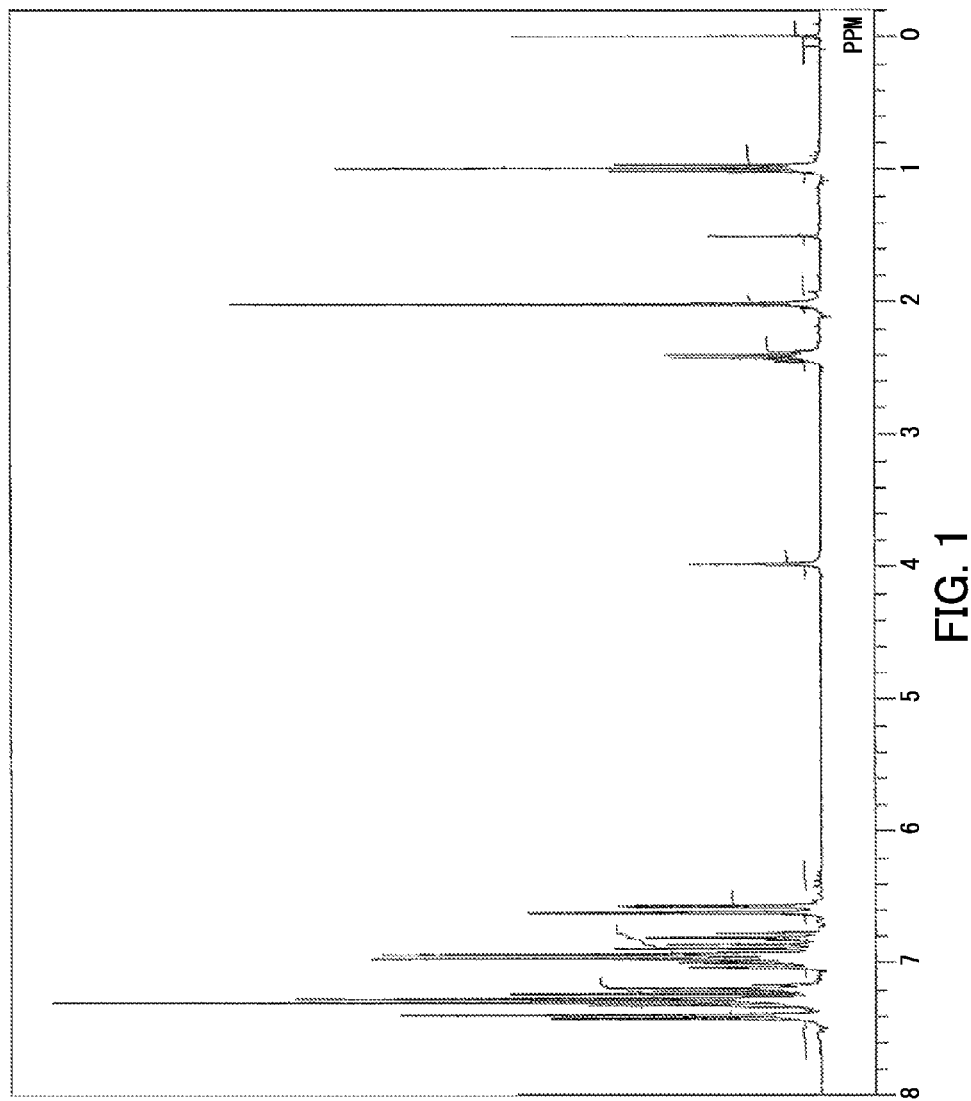
FIG. 1 shows a $^1$H-NMR spectrum of a triarylamine derivative represented by formula (H-1) according to a first embodiment of the present disclosure.

Hereinafter, embodiments of the present disclosure will be described in detail. Note that, however, the present disclosure is not in any way limited by the following embodiments. The present embodiments can be altered as appropriate within a range of the object of the present disclosure. Although explanation is omitted as appropriate in some instances in order to avoid repetition, such omission does not limit the essence of the present disclosure.

Hereinafter, note that in the present description, the term "-based" may be appended to the name of a chemical compound in order to form a generic name encompassing both the chemical compound itself and derivatives thereof. When the term "-based" is appended to the name of a chemical compound used in the name of a polymer, the term indicates that a repeating unit of the polymer originates from the chemical compound or a derivative thereof. Further, reactions represented by chemical formulae (R-1) to (R-8) may be referred to as reactions (R-1) to (R-8) respectively. Further, an application liquid for charge generating layer formation, an application liquid for charge transport layer formation, an application liquid for single-layer type photosensitive layer formation, and an application liquid for undercoat layer formation may be referred to as an application liquid for a charge generating layer, an application liquid for a charge transport layer, an application liquid for a single-layer photosensitive layer, and an application liquid for an undercoat layer.

Hereinafter, an halogen atom, an alkyl group having a carbon number of at least 1 and no greater than 6, an alkyl group having a carbon number of at least 1 and no greater than 4, an alkoxy group having a carbon number of at least 1 and no greater than 6, an aryl group having a carbon number of at least 6 and no greater than 14, and an alkylene group having a carbon number of at least 1 and no greater than 6 respectively mean the following, unless otherwise specified.

Examples of the halogen atom include fluorine (a fluoro group), chlorine (a chloro group), and bromine (a bromo group).

The alkyl group having a carbon number of at least 1 and no greater than 6 is a straight-chain or branched-chain unsubstituted alkyl group having a carbon number of at least 1 and no greater than 6. Examples of the alkyl group having a carbon number of at least 1 and no greater than 6 include a methyl group, an ethyl group, an n-propyl group, an isopropyl group, an n-butyl group, a sec-butyl group, a tert-butyl group, a pentyl group, an isopentyl group, a neopentyl group, and a hexyl group.

The alkyl group having a carbon number of at least 1 and no greater than 4 is a straight-chain or branched-chain, unsubstituted alkyl group having a carbon number of at least 1 and no greater than 4. Examples of the alkyl group having a carbon number of at least 1 and no greater than 4 include a methyl group, an ethyl group, a propyl group, an isopropyl group, an n-butyl group, a sec-butyl group, and a tert-butyl group.

The alkoxy group having a carbon number of at least 1 and no greater than 6 is a straight-chain or branched-chain, unsubstituted alkoxy group having a carbon number of at least 1 and no greater than 6. Examples of the alkoxy group having a carbon number of at least 1 and no greater than 6 include a methoxy group, an ethoxy group, an n-propoxy group, an isopropoxy group, an n-butoxy group, a sec-butoxy group, a tert-butoxy group, a pentyloxy group, an isopentyloxy group, a neopentyloxy group, and a hexyloxy group.

Examples of the aryl group having a carbon number of at least 6 and no greater than 14 include an unsubstituted aromatic single-ring hydrocarbon group having a carbon number of at least 6 and no greater than 14, an unsubstituted aromatic condensed double-ring hydrocarbon group having a carbon number of at least 6 and no greater than 14, and an unsubstituted aromatic condensed triple-ring hydrocarbon group having a carbon number of at least 6 and no greater than 14. Examples of the aryl group having a carbon number of at least 6 and no greater than 14 include a phenyl group, a naphthyl group, an anthryl group, and a phenanthryl group.

The alkylene group having a carbon number of at least 1 and no greater than 6 is a straight-chain or branched-chain, unsubstituted alkylene group having a carbon number of at least 1 and no greater than 6. Examples of the alkylene group having a carbon number of at least 1 and no greater than 6 include a methylene group, an ethylene group, an n-propylene group, a methylethylene group, an n-butylene group, a 1-methylpropylene group, a 2-methylpropylene group, a 1,1-dimethylethylene group, a 1,2-dimethylethylene group, a propylmethylene group, an ethyl methyl methylene group, a pentylene group, and a xylene group.

<First Embodiment: Triarylamine Derivative>

The first embodiment of the present disclosure refers to a triarylamine derivative. The triarylamine derivative of the present disclosure is represented by general formula (1) below.

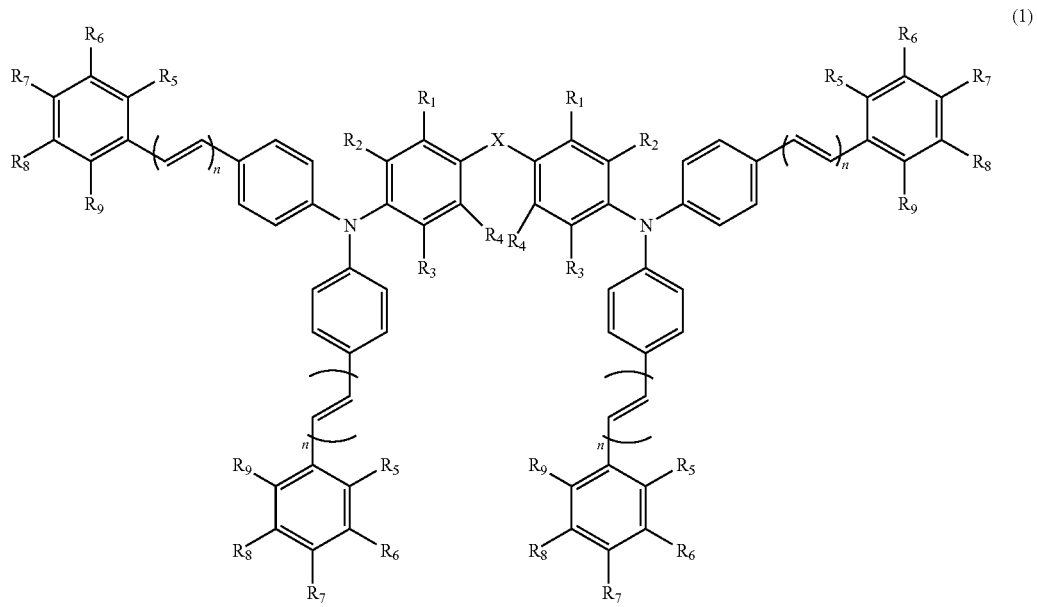

In the general formula (1), $R_1$, $R_2$, $R_4$, $R_5$, $R_6$, $R_7$, $R_8$, and $R_9$ each represent, independently from one another, a hydrogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 14. $R_3$ represents an alkyl group having a carbon number of at least 1 and no greater than 4. X represents an alkylene group having a carbon number of at least 1 and no greater than 6 or an oxygen atom. The symbol n represents an integer of at least 1 and no greater than 3.

The triarylamine derivative represented by the general formula (1) (hereinafter, may be referred to as a compound (1)) can improve electric characteristics of the electrophotographic photosensitive member (hereinafter, may be referred to as a photosensitive member). The reason for the above is thought to be as follows.

In the compound (1), three substituents bond to each of two nitrogen atoms. One of the three bonding substituents has a greatly different structure than the other two. As a result, asymmetry of the structure of the compound (1) increases. Thus, the compound (1) is easily dissolved in a solvent for forming a photosensitive layer, which makes it easy to obtain a photosensitive layer in which the compound (1) is uniformly dispersed. As a result, the electric characteristics of the photosensitive member are thought to improve.

In the compound (1), each of two phenyl groups bonding to the X has an alkyl group (corresponding to $R_3$) having a carbon number of at least 1 and no greater than 4. Having such a structure, the compound (1) is easily dissolved in the solvent for forming a photosensitive layer. As a result, a photosensitive layer can easily be obtained in which the compound (1) is uniformly dispersed. As a result, the electric characteristics of the photosensitive layer are thought to improve.

Further, two triphenylamine portions are boned together at the X in the compound (1). This consequently makes it difficult to parallely arrange a surface formed by one of the triphenylamine portions and a surface formed by another of the triphenylamine portions. Thus, it is difficult for the compounds (1) to be densely stacked on each other in the photosensitive layer. This consequently makes it difficult to cause intermolecular hydrogen bonding between one compound (1) and another compound (1). As a result, it is thought that the photosensitive layer is hardly crystalized and the electric characteristics of the photosensitive member improve.

The alkyl group having a carbon number of at least 1 and no greater than 6 and represented by $R_1$, $R_2$, and $R_4$ to $R_9$ in the general formula (1) is preferably an alkyl group having a carbon number of at least 1 and no greater than 4 and more preferably a methyl group or an ethyl group. The alkyl group having a carbon number of at least 1 and no greater than 6 and represented by $R_1$, $R_2$, and $R_4$ to $R_9$ may optionally be substituted. Examples of a substituent included in the alkyl group having a carbon number of at least 1 and no greater than 6 include a halogen atom, an alkoxy group having a carbon number of at least 1 and no greater than 6, and an aryl group having a carbon number of at least 6 and no greater than 14. No limitations are placed on the number of substituents, but the number is preferably no greater than three.

As the alkoxy group having a carbon number of at least 1 and no greater than 6 and represented by $R_1$, $R_2$, and $R_4$ to $R_9$ in the general formula (1), an alkoxy group having a carbon number of at least 1 and no greater than 3 is preferable. The alkoxy group having a carbon number of at least 1 and no greater than 6 and represented by $R_1$, $R_2$, and $R_4$ to $R_9$ may optionally be substituted. Examples of a substituent included in the alkoxy group having a carbon number of at least 1 and no greater than 6 include a halogen atom, an alkoxy group having a carbon number of at least 1 and no greater than 6, and an aryl group having a carbon number of at least 6 and no greater than 14. No limitations are placed on the number of substituents, but the number is preferably no greater than three.

As the aryl group having a carbon number of at least 6 and no greater than 14 and represented by $R_1$, $R_2$, and $R_4$ to $R_9$ in the general formula (1), a monocyclic aromatic hydrocarbon group having a carbon number of at least 6 and no greater than 14 is preferable, and a phenyl group is more preferable. The aryl group having a carbon number of at least 6 and no greater than 14 and represented by $R_1$, $R_2$, and $R_4$ to $R_9$ may optionally be substituted. Examples of a substituent included in the aryl group having a carbon number of at least 6 and no greater than 14 include a halogen atom, an alkyl group having a carbon number of at least 1 and no greater than 6, an alkoxy group having a carbon number of at least 1 and no greater than 6, and an aryl group having a carbon number of at least 6 and no greater than 14. No limitations are placed on the number of substituents, but the number is preferably no greater than three.

To improve the electric characteristics of the photosensitive member, $R_1$, $R_2$, and $R_4$ to $R_9$ each preferably represent, independently from one another, a hydrogen atom or an alkyl group having a carbon number of at least 1 and no greater than 6.

To improve the electric characteristics of the photosensitive member, $R_1$, $R_4$, $R_5$, $R_6$, $R_8$, and $R_9$ each preferably represent a hydrogen atom.

To improve the electric characteristics of the photosensitive member, $R_2$ and $R_7$ each more preferably represent, independently from each other, a hydrogen atom or an alkyl group having a carbon number of at least 1 and no greater than 6, even more preferably represent a hydrogen atom or an alkyl group having a carbon number of at least 1 and no greater than 4, and still even more preferably represent a hydrogen atom, a methyl group, or an ethyl group.

As the alkyl group having a carbon number of at least 1 and no greater than 4 and represented by $R_3$ in the general formula (1), a methyl group or an ethyl group is preferable, and the methyl group is more preferable.

As the alkylene group having a carbon number of at least 1 and no greater than 6 and represented by X in the general formula (1), an alkylene group having a carbon number of at least 1 and no greater than 3 is preferable, and a methylene group or an n-propylene group is more preferable.

To improve the electric characteristics of the photosensitive member, X represents preferably an alkylene group having a carbon number of at least 1 and no greater than 3 or an oxygen atom, more preferably a methylene group, an n-propylene group, or an oxygen atom, and even more preferably the methylene group or the oxygen atom.

In the general formula (1), n represents an integer of at least 1 and no greater than 3. The symbol n represents preferably 1 or 2, and more preferably 2. When n is 1 or 2, a molecular structure of the compound (1) is enlarged to an appropriate level, and a distance (hopping distance) between an electron cloud of one compound (1) present in the photosensitive layer and an electron cloud of another compound (1) in vicinity of the aforementioned compound (1) tends to decrease. As a result, it is through that movement characteristics of a hole between the compounds (1) improves, and thus the electric characteristics of the photosensitive member improve.

To improve the electric characteristics of the photosensitive member, a compound (1) is preferable in which $R_1$ to $R_9$, X, and n represent the following. $R_1$, $R_2$, $R_4$, $R_5$, $R_6$, $R_7$, $R_8$, and $R_9$ each represent, independently from one another, a hydrogen atom or an alkyl group having a carbon number of at least 1 and no greater than 6. $R_3$ represents an alkyl group having a carbon number of at least 1 and no greater than 4. X represents an alkylene group having a carbon number of at least 1 and no greater than 3 or an oxygen atom. Symbol n represents 1 or 2. A photosensitive member with a photosensitive layer containing such a compound (1) is excellent in not only electric characteristics but also in abrasion resistance. Further, in addition to such a compound (1), a resin having a repeating unit represented by the general formula (2) (hereinafter, referred to as a resin (2)) can be contained in the photosensitive layer to improve particularly the abrasion resistance and the electric characteristics of the photosensitive member. The resin (2) will be described later on.

To further improve the abrasion resistance of the photosensitive member, a compound (1) is preferable in which $R_1$ to $R_9$ represent the following. $R_1$, $R_4$, $R_5$, $R_6$, $R_7$, $R_8$, and $R_9$ each represent a hydrogen atom. $R_2$ represents an alkyl group having a carbon number of at least 1 and no greater than 4. $R_3$ represents an alkyl group having a carbon number of at least 1 and no greater than 4, which is different from that represented by $R_2$. Containing the resin (2), in addition to such a compound (1), in the photosensitive member can improve the abrasion resistance of the photosensitive member in particular.

To further improve the electric characteristics of the photosensitive member, a compound (1) is preferable in which $R_1$ to $R_9$, X, and n represent the following. $R_1$, $R_4$, $R_5$, $R_6$, $R_7$, $R_8$, and $R_9$ each represent a hydrogen atom. $R_2$ represents an alkyl group having a carbon number of at least 1 and no greater than 4. $R_3$ represents an alkyl group having a carbon number of at least 1 and no greater than 4, which is different from that represented by $R_2$. X represents an alkylene group having a carbon number of at least 1 and no greater than 3. Symbol n represents 2. Containing the resin (2), in addition to such a compound (1), in the photosensitive member can improve the abrasion resistance of the photosensitive member in particular.

When $R_2$ represents an alkyl group having a carbon number of at least 1 and no greater than 4 and $R_3$ represents an alkyl group having a carbon number of at least 1 and no greater than 4, which is different from the alkyl group represented by $R_2$, for example, $R_2$ represents an ethyl group, and $R_3$ represents an alkyl group other than an ethyl group, having a carbon number of at least 1 and no greater than 4 (more specifically, a methyl group, an n-propyl group, an isopropyl group, an n-butyl group, a sec-butyl group, or a tert-butyl group). To improve the electric characteristics and the abrasion resistance of the photosensitive member in particular, $R_2$ preferably represents an ethyl group and $R_3$ preferably represents a methyl group.

A content amount of the compound (1) as a hole transport material is preferably at least 10 parts by mass and no greater than 200 parts by mass and more preferably at least 20 parts by mass and no greater than 100 by mass relative to 100 parts by mass of a binder resin contained in a charge transport layer.

Detailed examples of the compound (1) include compounds represented by formulae (H-1) to (H-6) below. Hereinafter, the compounds represented by Formulae (H-1) to (H-6) may be respectively referred to as compounds (H-1) to (H-6). FIG. 1 illustrates a $^1$H-NMR spectrum of the compound (H-1).

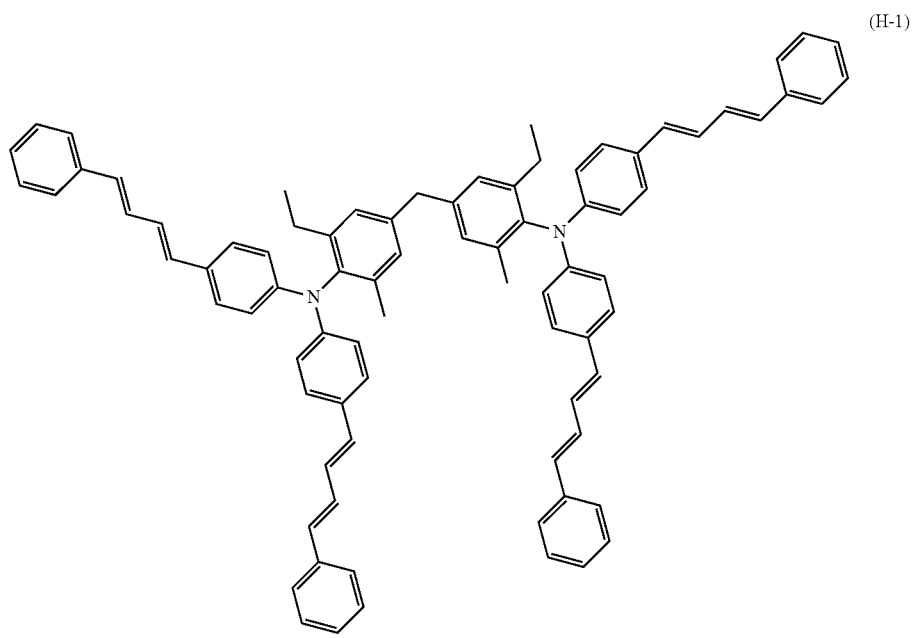

(H-1)

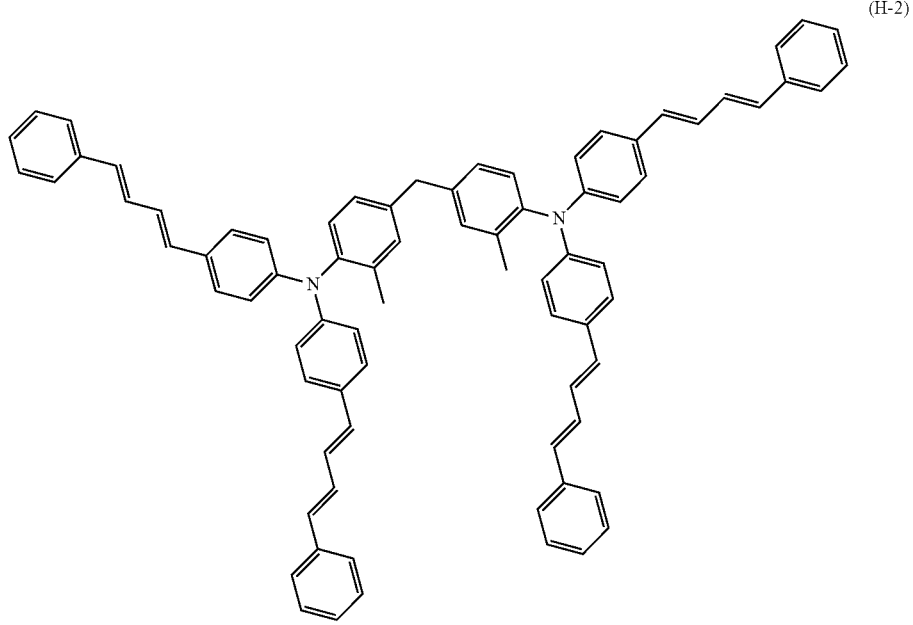
(H-2)
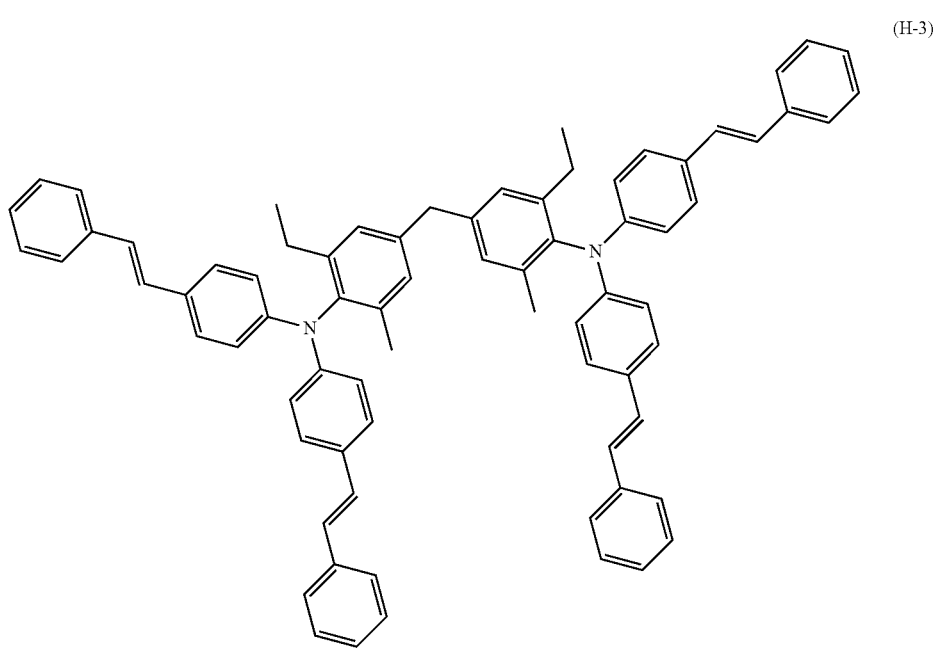
(H-3)

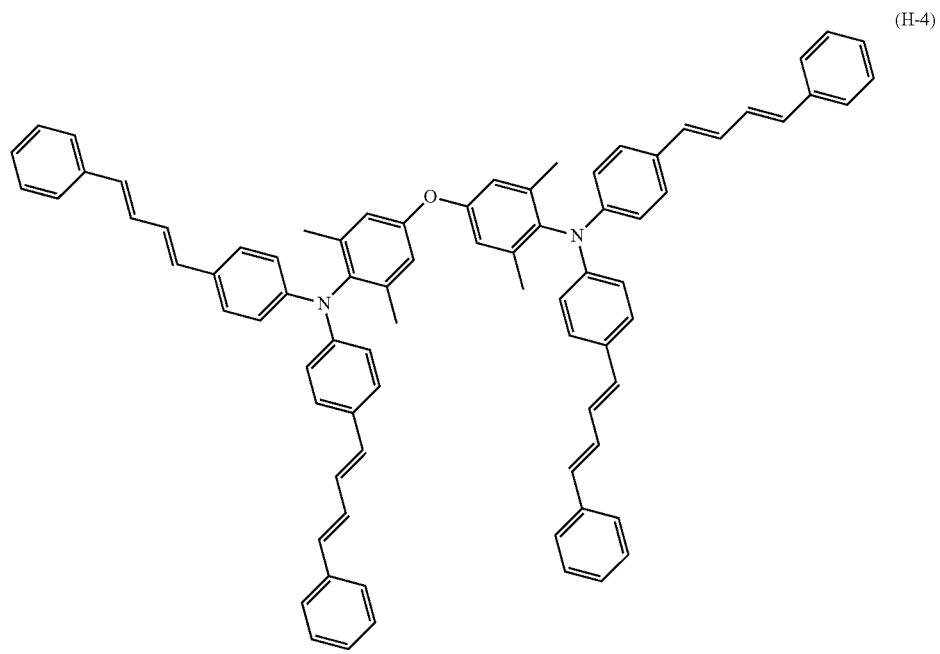
(H-4)
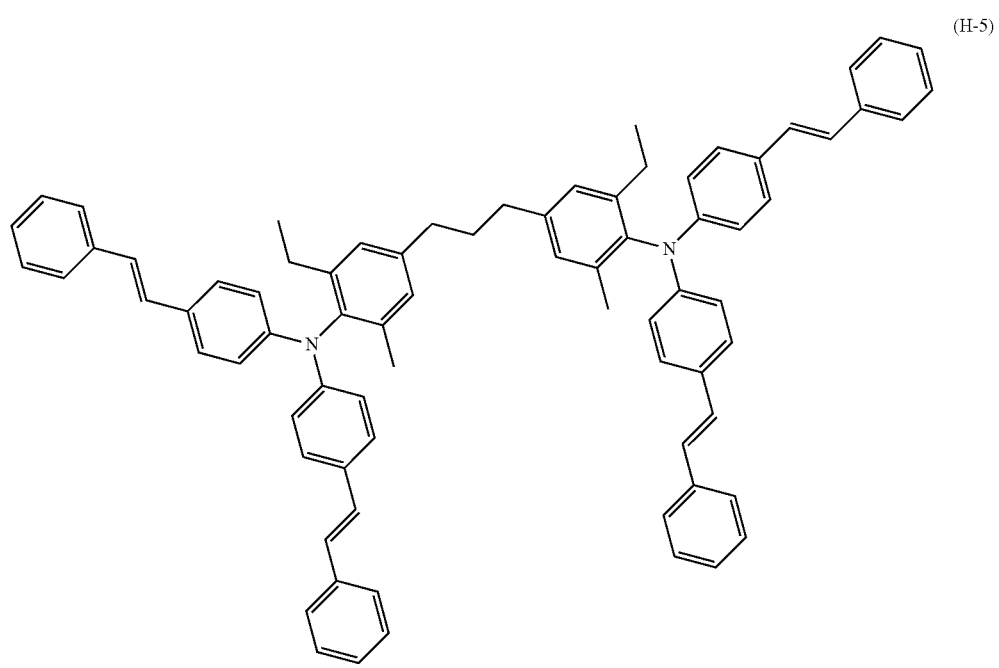
(H-5)

-continued

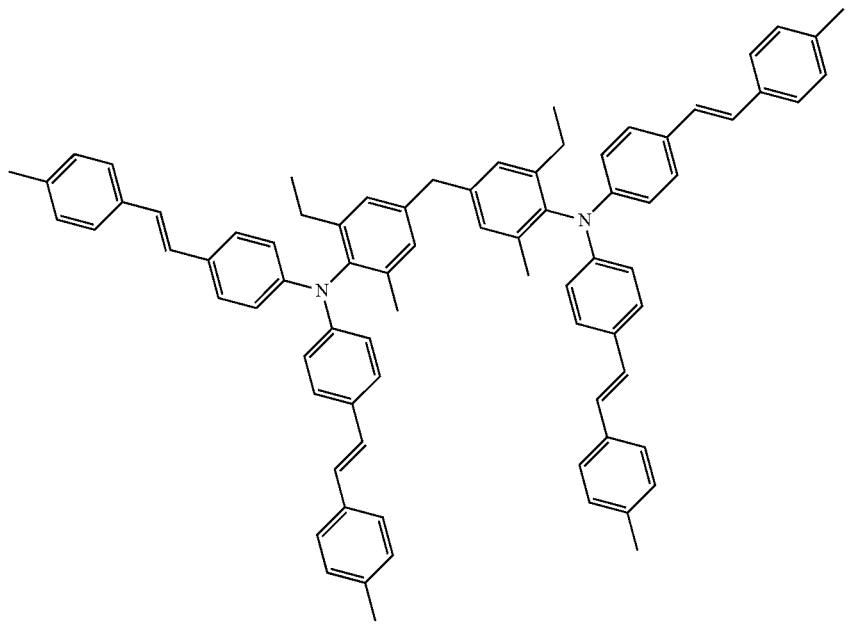

(H-6)

The compound (1) is, for example, produced in accordance with reactions (R-1) to (R-3) below or a method based thereon. In addition to these reactions, an appropriate process may be included when necessary.

In chemical formulae represented by the reactions (R-1) to (R-3), $R_1$, $R_2$, $R_3$, $R_4$, $R_5$, $R_6$, $R_7$, $R_8$, $R_9$, X, and n represent the same as $R_1$, $R_2$, $R_3$, $R_4$, $R_5$, $R_6$, $R_7$, $R_8$, $R_9$, X, and n in the general formula (1). Y represents a halogen atom.

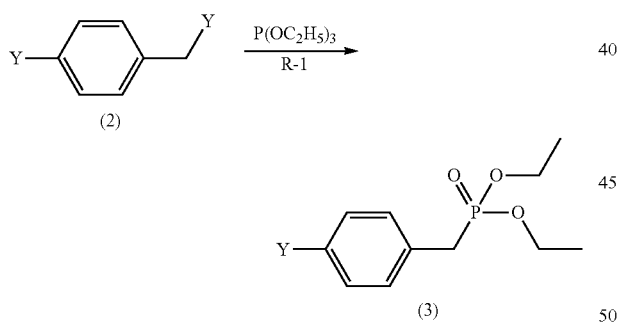

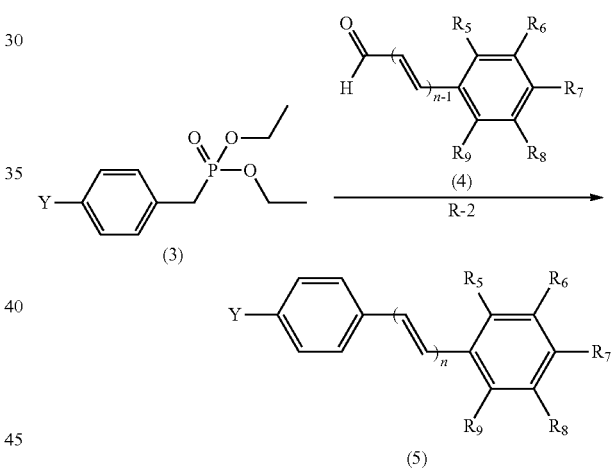

In the reaction (R-1), 1 equivalent of a compound (2) and 1 equivalent of triethyl phosphite are reacted to each other to obtain 1 equivalent of a compound (3). In the reaction (R-1), at least 1 mole and no greater than 2.5 moles of the triethyl phosphite is preferably added to 1 mole of the compound (2). Adding at least 1 mole of the triethyl phosphite to 1 mole of the compound (2) makes it easy to improve a yield ratio of the compound (3). On the other hand, adding no greater than 2.5 moles of the triethyl phosphite to 1 mole of the compound (2) makes it difficult for the unreacted triethyl phosphite to remain after the reaction and makes it easy to purify the compound (3). Reaction temperature in the reaction (R-1) is preferably at least 160° C. and no greater than 200° C. Reaction time in the reaction (R-1) is preferably at least two hours and no greater than ten hours.

In the reaction (R-2), 1 equivalent of the compound (3) and 1 equivalent of a compound (4) are reacted to each other to obtain 1 equivalent of a compound (5). The reaction (R-2) is Wittig reaction.

In the reaction (R-2), at least 1 mole and no greater than 10 moles of the compound (4) is preferably added to 1 mole of the compound (3). Adding 1 mole of the compound (4) to 1 mole of the compound (3) makes it easy to improve a yield ratio of the compound (5). Adding no greater than 10 moles of the compound (4) to 1 mole of the compound (3) makes it difficult for the unreacted compound (4) to remain and makes it easy to purify the compound (5).

The reaction (R-2) may be performed under presence of a base. Examples of the base include sodium alkoxides (more specifically a sodium methoxide and a sodium ethoxide), metal hydrides (more specifically, a sodium hydride or a potassium hydride), and a metal salt (more specifically an n-butyl lithium). Any one of these bases may be used alone or a combination of any two or more types of the bases may be used. An additive amount of the base is preferably at least 1 mole and no greater than 2 moles relative to 1 mole of the compound (3). The additive amount of at least 1 mole of the base can easily improve reactivity. On the other hand, the additive amount of no greater than 2 moles of the base makes it easy to control the reaction.

The reaction (R-2) may be performed in a solvent. Examples of the solvent include ethers (more specifically, tetrahydrofuran, a diethyl ether, and dioxane), halogenated hydrocarbons (more specifically, methylene chloride, chloroform, and dichloroethane) and aromatic hydrocarbons (more specifically, benzene and toluene).

Reaction temperature in the reaction (R-2) is preferably at least 0° C. and no greater than 50° C. Reaction time of the reaction (R-2) is preferably at least 2 hours and no greater than 24 hours.

In the reaction (R-3), at least 4 moles and no greater than 8 moles of the compound (5) is preferably added to 1 mole of the compound (6). Adding at least 4 moles of the compound (5) to 1 mole of the compound (6) makes it easy to improve a yield ratio of the compound (1). On the other hand, adding no greater than 8 moles of the compound (5) to 1 mole of the compound (6) makes it difficult for the unreacted compound (5) after the reaction to remain and makes it easy to purify the compound (1).

Reaction temperature in the reaction (R-3) is preferably at least 80° C. and no greater than 140° C. Reaction time of the reaction (R-3) is preferably at least 2 hours and no greater than 10 hours.

In the reaction (R-3), a palladium compound is preferably used as a catalyst. The use of the palladium compound tends to decrease activation energy in the reaction (R-3). As a

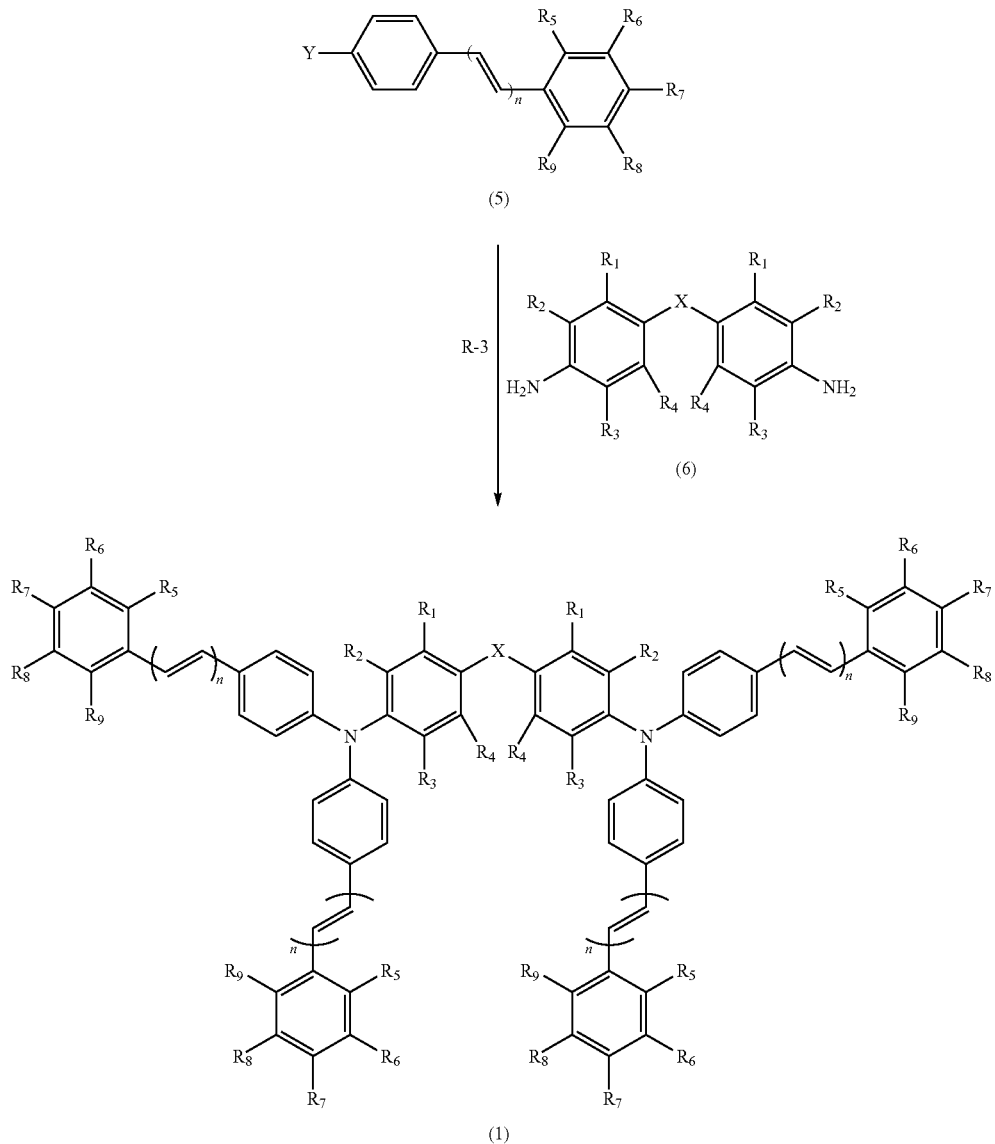

In the reaction (R-3), 4 equivalents of the compound (5) and 1 equivalent of a compound (6) are reacted to each other to obtain 1 equivalent of a compound (1). The reaction (R-3) is a coupling reaction.

result, it is thought that the yield ratio of the compound (1) can improve. Examples of the palladium compound include a tetravalent palladium compound, a bivalent palladium compound, and other palladium compounds. Examples of the tetravalent palladium compound include a hexachloro palladium (IV) sodium tetrahydrate and a hexachloro palladium(IV) potassium tetrahydrate. Examples of the bivalent palladium compounds include a palladium chloride (II), a palladium bromide (II), a paradium acetate (II), a palladium acetylacetate (II), a dichlorobis (benzonitrile) palladium (II), a dichlorobis (triphenylphosphine) palladium (II), a dichlorotetramine palladium (II), and a dichloro-(cyclooctа-1-5-diene) paradium (II). Examples of other palladium compounds include a tris (dibenzylideneacetone) dipalladium (0), a tris (dibenzylideneacetone) dipalladium chloroform complex (0), and a tetrakis (triphenylphosphine) palladium (0). Any one of the paradium compound may be used alone or a combination of any two or more types of the paradium compound may be used. An additive amount of the paradium compound is preferably at least 0.0005 moles and no greater than 20 moles and more preferably at least 0.001 moles and no greater than 1 mole relative to 1 mole of the compound (6).

The palladium compound may have a structure including a ligand. This consequently makes it easy to improve reactivity of the reaction (R-3). Examples of the ligand include tricyclohexylphosphine, triphenylphosphine, methyldiphenylphosphine, trifurylphosphine, tri (o-tolyl) phosphine, dicyclohexylphenylphosphine, tri (tert-butyl) phosphine, 2,2'-bis (diphenylphosphino)-1,1'-binaphthyl, and 2,2'-bis[(diphenylphosphino) diphenyl]ether. Any one of these ligands may be used alone or a combination of any two or more types of the ligands may be used. An additive amount of the ligand is preferably at least 0.0005 moles and no greater than 20 moles and more preferably at least 0.001 moles and no greater than 1 mole relative to 1 mole of the compound (6).

The reaction (R-3) is preferably performed under presence of a base. Consequently, it is thought that a hydrogen halide (for example, hydrogen chloride) generated in a reaction system is promptly neutralized, which permits an improvement in catalyst activity. As a result, it is thought that the yield ratio of the compound (1) can be improved. The base may be an inorganic base or an organic base. Preferable examples of the organic base include alkali metal alkoxides (more specifically, a sodium methoxide, a sodium ethoxide, a potassium methoxide, a potassium ethoxide, a lithium tert-butoxide, a sodium tert-butoxide, and a potassium tert-butoxide), among which the sodium tert-butoxide is more preferable. Examples of the inorganic base include a tripotassium phosphate and a caesium fluoride. When at least 0.0005 moles and no greater than 20 moles of a palladium compound is to be added to 1 mole of the compound (6), an additive amount of the base is preferably at least 1 mole and no greater than 50 moles and more preferably at least 1 mole and no greater than 30 moles.

The reaction (R-3) may be performed in a solvent. Examples of the solvent include xylene (more specifically, o-xylene), toluene, tetrahydrofuran, and dimethyl formamide.

The triarylamine derivative according to the present embodiment have been described above. When contained in the photosensitive layer of the photosensitive member, the triarylamine derivative according to the present embodiment can improve the electric characteristics of the photosensitive member. When contained in the photosensitive layer of the photosensitive member, the triarylamine derivative according to the present embodiment can also improve both the electric characteristics and abrasion resistance of the photosensitive member.

<Second Embodiment: Photosensitive Member>

The second embodiment relates to a photosensitive member. The photosensitive member may be a multi-layer type photosensitive member or a single-layer type photosensitive member. The photosensitive member includes a photosensitive layer including a charge generating material and a hole transport material. The hole transport material is the compound (1) according to the first embodiment.

<1. Multi-Layer Type Photosensitive Member>

Figure 2A:
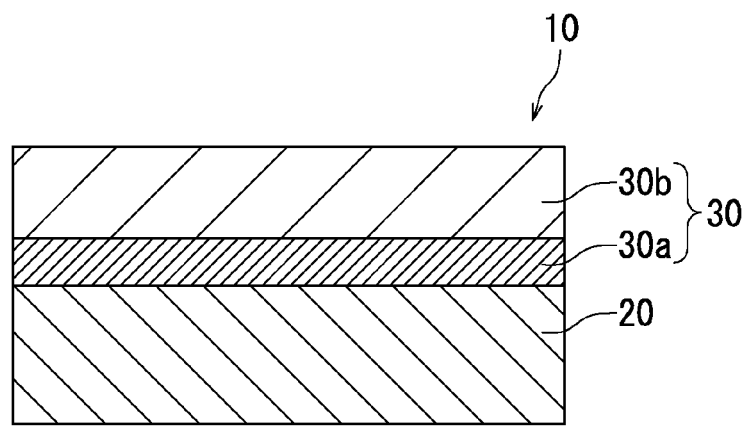
FIGS. 2A, 2B, an 2C are schematic cross-sectional views each illustrating one example of an electrophotographic photosensitive member according to a second embodiment of the present disclosure.
Figure 2B:
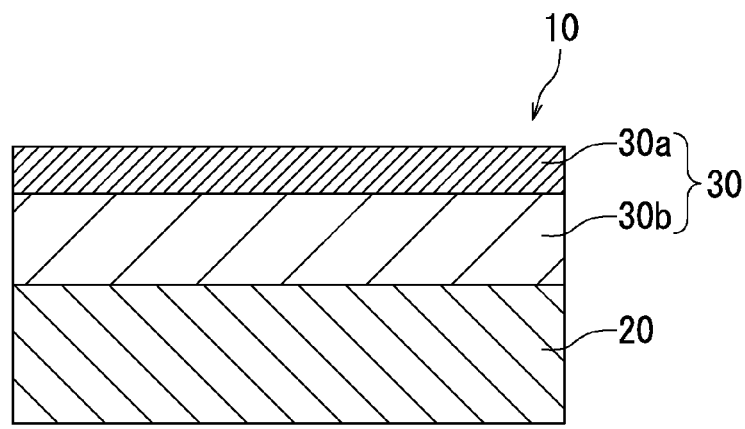
Figure 2C:
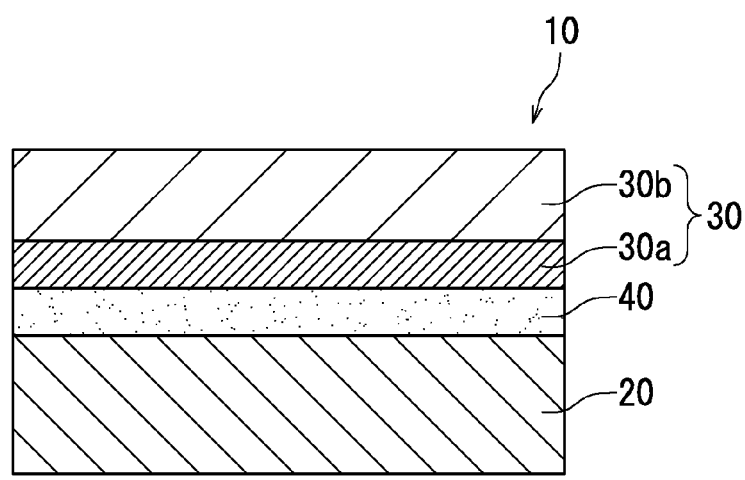

Hereinafter, with reference to FIGS. 2A to 2C, a structure of the photosensitive member 10 when the photosensitive member 10 is a multi-layer type photosensitive member will be described. FIGS. 2A to 2C are schematic cross-sectional views each illustrating the multi-layer type photosensitive member as one example of the photosensitive member 10 according to the present embodiment.

As illustrated in FIG. 2A, the multi-layer type photosensitive member as the photosensitive member 10 includes, for example, a conductive substrate 20 and a photosensitive layer 30. The multi-layer type photosensitive member includes a charge generating layer 30a and a charge transport layer 30b as the photosensitive layer 30.

As illustrated in FIG. 2B, in the multi-layer type photosensitive member as the photosensitive member 10, the charge transport layer 30b may be provided on the conductive substrate 20, and the charge generating layer 30a may be provided on the charge transport layer 30b. Note that the charge transport layer 30b typically has a larger film thickness than the charge generating layer 30a, and thus the charge transport layer 30b is more hardly broken than the charge generating layer 30a. Thus, to improve abrasion resistance of the multi-layer type photosensitive member, as illustrated in FIG. 2A, it is preferable that the charge generating layer 30a be provided on the conductive substrate 20 and the charge transport layer 30b be provided on the charge generating layer 30a.

As illustrated in FIG. 2C, the multi-layer type photosensitive member as the photosensitive member 10 may include the conductive substrate 20, the photosensitive layer 30, and an intermediate layer (underlying layer) 40. The intermediate layer 40 is included between the conductive substrate 20 and the photosensitive layer 30. A protective layer 50 (see FIG. 3C) may further be provided on the photosensitive layer 30.

No limitations are placed on thicknesses of the charge generating layer 30a and the charge transport layer 30b so long the thicknesses permits sufficient functions to be exerted. The thickness of the charge generating layer 30a is preferably at least 0.01 µm and no greater than 5 µm and more preferably at least 0.1 µm and 3 µm. The thickness of the charge transport layer 30b is preferably at least 2 µm and no greater than 100 µm and more preferably at least 5 µm and no greater than 50 µm.

The charge generating layer 30a included in the photosensitive layer 30 contains a charge generating material. The charge generating layer 30a may contain a binder resin for a charge generating layer (hereinafter may be referred to as a base resin). The charge generating layer 30a may contain any of various types of additives when necessary.

The charge transport layer 30b included in the photosensitive layer 30 contains a hole transport material. The charge transport layer 30b may contain a binder resin. The charge transport layer 30b may contain an electron acceptor compound and any of various types of additives when necessary. With reference to FIGS. 2A to 2C, the structure of the photosensitive member 10 when the photosensitive member 10 is a multi-layer type photosensitive member has been described above.

<2. Single-Layer Type Photosensitive Member>

Hereinafter, with reference to FIGS. 3A to 3C, a structure of the photosensitive member 10 when the photosensitive member 10 is a single-layer type photosensitive member will be described. FIG. 3 are schematic cross-sectional views illustrating the single-layer type photosensitive member as another example of the photosensitive member 10 according to the present embodiment.

Figure 3A:
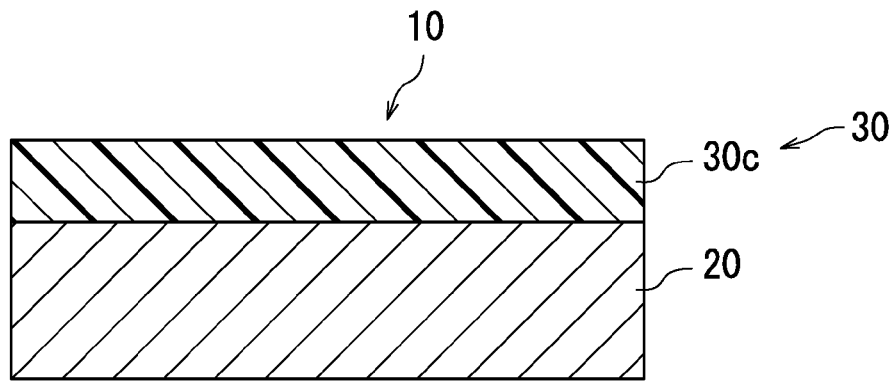
FIGS. 3A, 3B, and 3C are schematic cross-sectional views each illustrating another example of the electrophotographic photosensitive member according to the second embodiment of the present disclosure.

As illustrated in FIG. 3A, the single-layer type photosensitive member as the photosensitive member 10 includes, for example, a conductive substrate 20 and a photosensitive layer 30. The single-layer type photosensitive member as the photosensitive member 10 includes a single-layer type photosensitive layer 30c as the photosensitive layer 30. The single-layer type photosensitive layer 30c is a one-layer photosensitive layer 30.

Figure 3B:
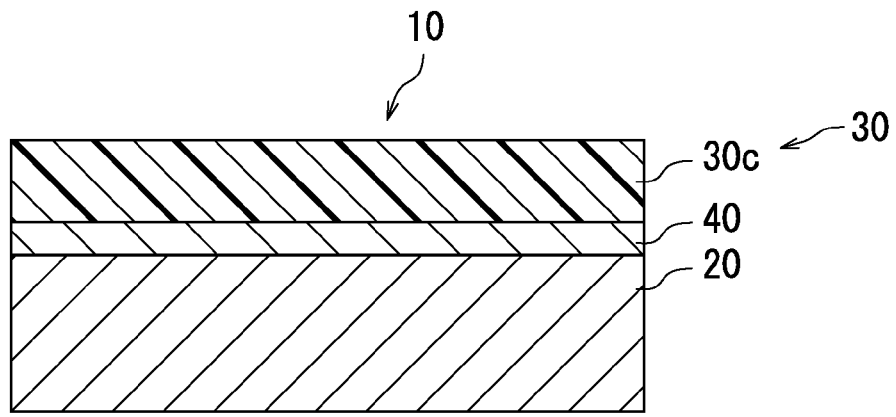
Figure 3C:
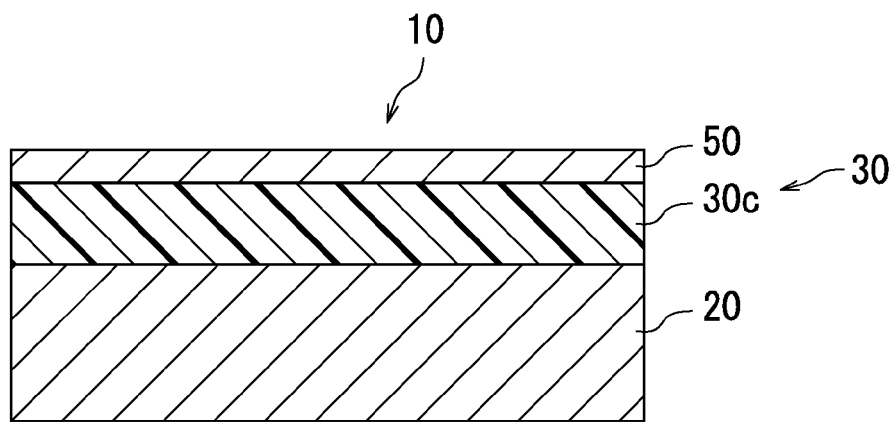

As illustrated in FIG. 3B, the single-layer type photosensitive member as the photosensitive member 10 may include a conductive substrate 20, the single-layer type photosensitive layer 30c, and an intermediate layer (underlying layer) 40. The intermediate layer 40 is provided between the conductive substrate 20 and the photosensitive layer 30. As illustrated in FIG. 3C, a protective layer 50 may be provided on the single-layer type photosensitive layer 30c.

No limitations are placed on a thickness of the single-layer type photosensitive layer 30c so long as the thickness permits sufficient functions as the single-layer type photosensitive member to be exerted. The thickness of the single-layer type photosensitive layer 30c is preferably at least 5 μm and no greater than 100 μm and more preferably at least 10 μm and no greater than 50 μm.

The single-layer type photosensitive layer 30c as the photosensitive layer 30 contains a charge generating material and a hole transport material. The single-layer type photosensitive layer 30c may further contain at least one of an electron transport material and a binder resin. The single-layer type photosensitive layer 30c may contain any of various types of additives when necessary. That is, when the photosensitive member 10 is a single-layer type photosensitive member, the charge generating material, the hole transport material, and a component added when necessary (for example, the electron transport material, the binder resin, or the additive) are included in the one-layer photosensitive layer 30 (the single-layer type photosensitive layer 30c). With reference to FIGS. 3A to 3C, the structure of the photosensitive member 10 when the photosensitive member 10 is a single-layer type photosensitive member has been described above.

Next, elements of the multi-layer type photosensitive member and the single-layer type photosensitive member each serving as the photosensitive member will be described.

<3. Conductive Substrate>

No limitations are placed on the conductive substrate so long as the conductive substrate is used as a conductive substrate of a photosensitive member. The conductive substrate may have at least a surface part formed of a conductive material. One example of the conductive substrate is a conductive substrate formed of a conductive material. Another example of the conductive substrate is a conductive substrate coated with a conductive material. Examples of the conductive material include aluminum, iron, copper, tin, platinum, silver, vanadium, molybdenum, chromium, cadmium, titanium, nickel, palladium, indium, stainless steel, and brass. Any one of these conductive materials may be used alone or a combination (for example, as an alloy) of any two or more types of the conductive materials may be used.

Of these conductive materials, the aluminum or the aluminum alloy is preferable since movement of changes from the photosensitive layer to the conductive substrate is favorable with the aluminum or the aluminum alloy.

A shape of the conductive substrate is appropriately selected in accordance with a structure of an image forming apparatus. Examples of the shape of the conductive substrate include a sheet-like shape and a drum-like shape. The conductive substrate has a thickness appropriately selected in accordance with the shape of the conductive substrate.

<4. Hole Transport Material>

The photosensitive layer contains, as the hole transport material, the compound (1) according to the first embodiment. When the photosensitive member is a multi-layer type photosensitive member, the charge transport layer contains the compound (1) as the hole transport material. When the photosensitive member is a single-layer type photosensitive member, the single-layer type photosensitive layer contains the compound (1) as the hole transport material. Containing the compound (1) in the photosensitive layer can improve the electric characteristics of the photosensitive member, as described in the first embodiment.

When the photosensitive member is a multi-layer type photosensitive member, a content amount of the compound (1) as the hole transport material is preferably at least 10 parts by mass and no greater than 200 parts by mass and more preferably at least 20 parts by mass and no greater than 100 parts by mass relative to 100 parts by mass of the binder resin contained in the charge transport layer.

When the photosensitive member is a single-layer type photosensitive member, a content amount of the compound (1) as the hole transport material is preferably at least 10 parts by mass and no greater than 200 parts by mass, more preferably at least 10 parts by mass and no greater than 100 parts by mass, and even more preferably at least 10 parts by mass and no greater than 75 parts by mass relative to 100 parts by mass of the binder resin contained in the single-layer type photosensitive member.

The charge transport layer or the single-layer type photosensitive layer may further contain another hole transport material in addition to the compound (1). As another hole transport material, for example, a nitrogen containing cyclic compound or a condensed polycyclic compound other than the compound (1) can be used. Examples of the nitrogen containing cyclic compound and the condensed polycyclic compound include diamine derivatives other than the compound (1) (for example, an N, N,N',N'-tetraphenylphenylenediamine derivative, an N,N,N',N'-tetraphenylnaphtylenediamine derivative, and an N,N,N',N'-tetraphenylphenanthrylenediamine derivative), oxadiazole-based compounds (for example, 2,5-di(4-methylaminophenyl)-1,3,4-oxadiazole), styryl compounds (for example, 9-(4-diethylaminostyryl) anthracene), carbazole compounds (for example, polyvinyl carbazole), organic polysilane compounds, pyrazoline-based compounds (for example, 1-phenyl-3-(p-dimethylaminophenyl) pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. A content amount of the compound (1) is preferably at least 80% by mass, more preferably at least 90% by mass, and even more preferably 100% by mass relative to a total mass of the hole transport material.

<5. Charge Generating Material>

When the photosensitive member is a multi-layer type photosensitive member, the charge generating layer includes a charge generating material. When the photosensitive member is a single-layer type photosensitive member, the single-layer type photosensitive layer includes a charge generating material.

No limitations are placed on the charge generating material so long as the charge generating material is provided for a photosensitive member. Examples of the charge generating material include phthalocyanine-based pigments, perylene-based pigments, a bisazo pigment, a tris-azo pigment, a dithioketopyrrolopyrrole pigment, a metal-free naphthalocyanine pigment, a metal naphthalocyanine pigment, a squaraine pigment, an indigo pigment, an azulenium pigment, a cyanine pigment, powders of inorganic photoconductive materials (for example, selenium, selenium-tellurium, selenium-arsenic, cadmium sulfide, and amorphous silicon), a pyrylium pigment, anthanthrone-based pigments, triphenylmethane-based pigments, threne-based pigments, toluidine-based pigments, pyrazoline-based pigments, and quinacridone-based pigments. Any one of the charge generating materials may be used alone or a combination of any two or more types of the charge generating materials may be used.

Examples of the phthalocyanine-based pigments include metal-free phthalocyanine represented by chemical formula (C-1) and metal phthalocyanine. Examples of the metal phthalocyanine include titanyl phthalocyanine represented by chemical formula (C-2), hydroxygallium phthalocyanine, and chlorogallium phthalocyanine. The phthalocyanine-based pigments may be crystalline or non-crystalline. No limitations are placed on a crystal structure of the phthalocyanine-based pigments (for example, a type, a β type, a Y type, V type, and II type), and phthalocyanine-based pigmented having various crystal structures are used.

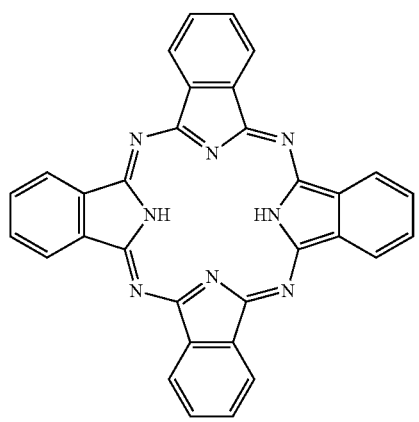

(C-1)

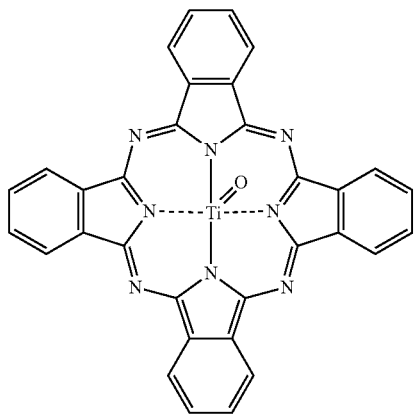

(C-2)

Examples of a crystal of the metal-free phthalocyanine include an X form crystal of the metal-free phthalocyanine (hereinafter, may be referred to as X-form metal-free phthalocyanine). Examples of the crystal of the titanyl phthalocyanine include an α type, a β type, and a Y type crystal of titanyl phthalocyanine (hereinafter, may be referred to as a α-form, a β-form, and a Y-form titanyl phthalocyanine). As the crystal of the hydroxygallium phthalocyanine, a V-form crystal of hydroxygallium phthalocyanine is provided. As the crystal of the chlorogallium phthalocyanine, a II-form crystal of chlorogallium phthalocyanine is provided.

For example, for a digital optical image forming apparatus (for example, a laser beam printer or a facsimile using a light source such as a semiconductor laser), a photosensitive member is preferably used which has sensitivity in a wavelength range of at least 700 nm. A high quantum yield is provided in the wavelength range of at least 700 nm, and thus for the charge generating material, the phthalocyanine-based pigments are preferable, the metal-free phthalocyanine or titanyl phthalocyanine is more preferable, and the X-form metal-free phthalocyanine or the Y-form titanyl phthalocyanine is even more preferable. To improve the electric characteristics in particular when the photosensitive layer includes the compound (1) as the hole transport material, the Y-form titanyl phthalocyanine (i.e. titanyl phthalocyanine having a y-form crystal structure) is more preferable as the charge generating material.

The Y-form titanyl phthalocyanine, for example, has a main peak at a Bragg angle of 27.2° (2θ±0.2°) in a CuKα characteristic X-ray diffraction spectrum. The main peak in the CuKα characteristic X-ray diffraction spectrum, in a range where the Bragg angle (2θ±0.2°) is at least 3° and no greater than 40°, is a peak having largest or second largest strength.

(CuKα Characteristic X-Ray Diffraction Spectrum Measurement Method)

One example of the CuKα characteristic X-ray diffraction spectrum measurement method will be described. A sample (titanyl phthalocyanine) is filled in a sample holder of an X-ray diffractometer (for example, "RINT (registered Japanese trademark) 1100" produced by Rigaku Corporation), and an X-ray diffraction spectrum is measured with an X-ray tube valve Cu, a tube voltage of 40 kV, a tube current of 30 mA, and a wavelength of 1.542 Å of a CuKα characteristic X-ray. A measurement range (2θ) is, for example, at least 3° and no greater than 40° (with a start angle of 3° and a stop angle of 40°) and a scan speed is, for example, 10°/min.

For a photosensitive member applied to an image forming apparatus using a short-wavelength laser light source (for example, a laser light source having a wavelength of at least 350 nm and no greater than 550 nm), an anthanthrone-based pigment is preferably used as the charge generating material.

When the photosensitive member is a multi-layer type photosensitive member, a content amount of the charge generating material is preferably at least 5 parts by mass and no greater than 1000 parts by mass and more preferably at least 30 parts by mass and no greater than 500 parts by mass relative to 100 parts by mass of the base resin contained in the charge generating layer.

When the photosensitive member is a single-layer type photosensitive member, a content amount of the charge generating material is preferably at least 0.1 parts by mass and no greater than 50 parts by mass, more preferably at least 0.5 parts by mass and no greater than 30 parts by mass, and even more preferably at least 0.5 parts by mass and no greater than 4.5 parts by mass relative to 100 parts by mass of the binder resin contained in the single-layer type photosensitive layer.

<6. Electron Transport Material and Electron Acceptor Compound>

When the photosensitive member is a multi-layer type photosensitive member, the charge transport layer may include an electron acceptor compound when necessary. Consequently, hole transport capability of the hole transport material tends to improve. On the other hand, when the photosensitive member is a single-layer type photosensitive member, the single-layer type photosensitive layer may include an electron transport material when necessary. Consequently, the single-layer type photosensitive layer can transport electrons, making it easy to provide the single-layer type photosensitive layer with bipolar characteristics.

Examples of the electron transport material and the electron acceptor compound include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of the quinone-based compounds include diphenoquinone-based compounds, azoquinone-based compounds, anthraquinone-based compounds, naphthoquinone-based compounds, nitroanthraquinone-based compounds, and dinitroanthraquinone-based compounds. Any one of the electron transport materials may be used alone or a combination of any two or more types of the electron transport materials may be used.

Examples of the electron transport material or the electron acceptor include a compound represented by general formula (7) or (8).

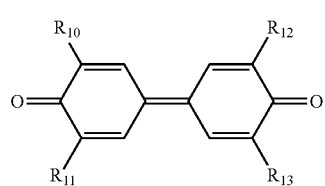

(7)

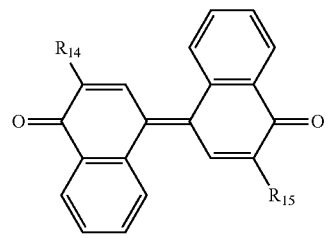

(8)

In the general formulae (7) and (8), $R_{10}$ to $R_{15}$ each represent, independently from one another, a hydrogen atom, a cyano group, an optionally substituted alkyl group, an optionally substituted alkenyl group, an optionally substituted alkoxy group, an optionally substituted alkoxycarbonyl group, an optionally substituted aryl group, and an optionally substituted heterocyclic group.

The alkyl group represented by $R_{10}$ to $R_{15}$ in the general formulae (7) and (8) is, for example, an alkyl group having a carbon number of at least 1 and no greater than 6. The alkyl group having a carbon number of at least 1 and no greater than 6 is preferably an alkyl group having a carbon number of at least 1 and no greater than 5 and more preferably a methyl group, a tert-butyl group, or a 1,1-dimethyl propyl group. The alkyl group may optionally be substituted. Examples of a substituent include a halogen atom, a hydroxyl group, an alkoxy group having a carbon number of at least 1 and no greater than 6, a further optionally substituted aryl group having a carbon number of at least 6 and no greater than 14, and a cyano group. No limitations are placed on the number of substituents, but the number is preferably no greater than three. Examples of the substituent further included in the substituted aryl group which has a carbon number of at least 6 and no greater than 14 and which is included in the alkyl group include a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group obtained by bonding together a carbonyl group and an alkyl group having a carbon number of at least 1 and no greater than 6), a benzoyl group, a phenoxy group, an alkoxycarbonyl group having a carbon number of at least 2 and no greater than 7 (a group obtained by bonding together a carbonyl group and an alkoxy group having a carbon number of at least 1 and no greater than 6), and a phenoxycarbonyl group.

The alkenyl group represented by $R_{10}$ to $R_{15}$ in the general formulae (7) and (8) is, for example, a straight-chain or branched-chain, unsubstituted alkenyl group having a carbon number of at least 2 and no greater than 6. The alkenyl group having a carbon number of at least 2 and no greater than 6 has, for example, at least one double bond and no greater than three double bonds. Examples of the alkenyl group having a carbon number of at least 2 and no greater than 6 include a vinyl group, a propenyl group, a butenyl group, a pentenyl group, a pentadienyl group, a hexenyl group, and a hexadienyl group. The alkenyl group may optically be substituted. Examples of a substituent include a halogen atom, a hydroxyl group, an alkoxy group having a carbon number of at least 1 and no greater than 6, an aryl group or having a carbon number of at least 6 and no greater than 14, and a cyano group. No limitations are placed on the number of substituents, but the number is preferably no greater than three.

The alkoxy group represented by $R_{10}$ to $R_{15}$ in the general formulae (7) and (8) is, for example, an alkoxy group having a carbon number of at least 1 and no greater than 6. The alkoxy group having a carbon number of at least 1 and no greater than 6 is preferably an alkoxy group having a carbon number of at least 1 and no greater than 3 and more preferably a methoxy group. The alkoxy group may optionally be substituted. Examples of a substituent include a halogen atom, a hydroxyl group, an alkoxy group having a carbon number of at least 1 and no greater than 6, an aryl group having a carbon number of at least 6 and no greater than 14, and a cyano group. The substituent is preferably a phenyl group. No limitations are placed on the number of substituents, but the number is preferably no greater than three and more preferably one.

The alkoxycarbonyl group represented by $R_{10}$ to $R_{15}$ in the general formulae (7) and (8) is, for example, an alkoxycarbonyl group having a carbon number of at least 2 and no greater than 7. The alkoxycarbonyl group having a carbon number of at least 2 and no greater than 7 is a group obtained by bonding together a carbonyl group and a straight-chain or branched-chain, unsubstituted alkoxy group having carbon number of at least 1 and no greater than 6. The alkoxycarbonyl group may optically be substituted. Examples of a substituent include a halogen atom, a hydroxyl group, an alkoxy group having a carbon number of at least 1 and no greater than 6, an aryl group having a carbon number of at least 6 and no greater than 14, and a cyano group. No limitations are placed on the number of substituents, but the number is preferably no greater than three.

The aryl group represented by $R_{10}$ to $R_{15}$ in the general formulae (7) and (8) is, for example, an aryl group having a carbon number of at least 6 and no greater than 14. As the aryl group having a carbon number of at least 6 and no greater than 14, a phenyl group is preferable. The aryl group may optically be substituted. Examples of a substituent include a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group obtained by bonding together a carbonyl group and an alkyl group having a carbon number of at least 1 and no greater than 6), a benzoyl group, a phenoxy group, an alkoxycarbonyl group having a carbon number of at least 2 and no greater than 7 (a group obtained by bonding together a carbonyl group and an alkoxy group having a carbon number of at least 1 and no greater than 6), a phenoxycarbonyl group, an aryl group having a carbon number of at least 6 and no greater than 14, and a biphenyl group. No limitations are placed on the number of substituents, but the number is preferably no greater than three.

Examples of the heterocyclic group represented by $R_{10}$ to $R_{15}$ in the general formulae (7) and (8) include a 5-membered or 6-membered, monocyclic heterocyclic group including at least one hetero atom selected from the group consisting of N, S, and O; a heterocyclic group obtained by condensing such monocyclic groups; and a heterocyclic group obtained by condensing such monocyclic groups and a 5- or 6-membered cyclic hydrocarbon group. When the heterocyclic group is a condensed cycle, the number of cycles included in the condensed cycle is preferably 2 or 3. The heterocyclic group may optically be substituted. Examples of a substituent that the heterocyclic group may have include a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group obtained by bonding together a carbonyl group and an alkyl group having a carbon number of at least 1 and no greater than 6), a benzoyl group, a phenoxy group, an alkoxycarbonyl group having a carbon number of at least 2 and no greater than 7 (a group obtained by bonding together a carbonyl group and an alkoxy group having a carbon number of at least 1 and no greater than 6), and a phenoxycarbonyl group. No limitations are placed on the number of substituents, but the number is preferably no greater than three.

When the photosensitive layer is a single-layer type photosensitive member and contains the compound (1) as the hole transport material in the single-layer type photosensitive layer, the single-layer type photosensitive layer preferably contains, as an electron transport material, a compound represented by the general formula (8) to further improve the electric characteristics of the photosensitive member.

As a detailed example of the compound represented by the general formula (7), a compound represented by chemical formula (E-2) is provided. As a detailed example of the compound represented by the general formula (8), a compound represented by chemical formula (E-1) is provided. Hereinafter, the compounds represented by chemical formulae (E-1) and (R-2) are respectively referred to as compounds (E-1) and (E-2).

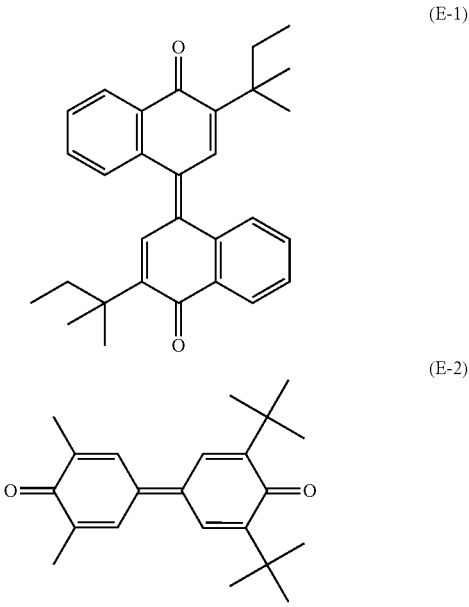

When the photosensitive member is a multi-layer type photosensitive member, a content amount of the electron acceptor compound is preferably at least 0.1 parts by mass and no greater than 20 parts by mass and more preferably at least 0.5 parts by mass and no greater than 10 parts by mass relative to 100 parts by mass of the binder resin contained in the charge transport layer.

When the photosensitive member is a single-layer type photosensitive member, a content amount of the electron transport material is preferably at least 5 parts by mass and no greater than 100 parts by mass, more preferably at least 10 parts by mass and no greater than 80 parts by mass, and even more preferably at least 30 parts by mass and no greater than 50 parts by mass relative to 100 parts by mass of the binder resin contained in the single-layer type photosensitive layer.

<7. Binder Resin>

When the photosensitive member is a multi-layer type photosensitive member, the charge transport layer contains a binder resin. When the photosensitive member is a single-layer type photosensitive member, the single-layer type photosensitive layer contains a binder resin.

Examples of the binder resin include a thermoplastic resin, a thermosetting resin, and a photocurable resin. Examples of the thermoplastic resin include a polycarbonate resin, a polyarylate resin, a styrene-butadiene copolymer, a styrene-acrylonitrile copolymer, a styrene-maleate copolymer, an acrylic acid polymer, a styrene-acrylate copolymer, a polyethylene resin, an ethylene-vinyl acetate copolymer, a chlorinated polyethylene resin, a polyvinyl chloride resin, a polypropylene resin, an ionomer resin, a vinyl chloride-vinyl acetate copolymer, an alkyd resin, a polyamide resin, an urethane resin, a polysulfone resin, a diallyl phthalate resin, a ketone resin, a polyvinyl butyral resin, a polyester resin, and a polyether resin. Examples of the thermosetting resin include a silicone resin, an epoxy resin, a phenolic resin, a urea resin, and a melamine resin. Examples of the photocurable resin include an epoxy acrylate (an acrylic acid adduct of an epoxy compound) and a urethane acrylate (an acrylic acid adduct of an urethane compound). Any one of these binder resins may be used alone or a combination of any two or more types of the binder resins may be used Of these resins, the polycarbonate resin is preferable since such a resin can provide a single-layer type photosensitive layer and a charge transport layer having excellent balance between workability, mechanical characteristics, optical characteristics, and abrasion resistance.

As the polycarbonate resin, the resin (2) is preferable. The resin (2) has a repeating unit represented by general formula (2) below.

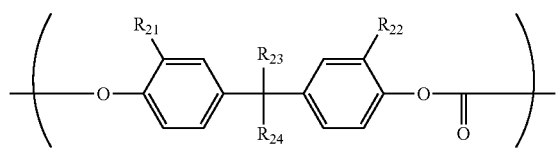

(2)

In the general formula (2), $R_{21}$ and $R_{22}$ each represent, independently from each other, a hydrogen atom, an alkyl group, or an aryl group. $R_{23}$ and $R_{24}$ each represent, independently from each other, a hydrogen atom, an alkyl group, or an aryl group.

Alternatively, $R_{23}$ and $R_{24}$ bond to each other to represent (to form) a cycloalkylidene group. That is, $R_{23}$ and $R_{24}$ may integrally represent a cycloalkylidene group while bonding to each other.

When the photosensitive member is a multi-layer type photosensitive member, containing the compound (1) and the resin (2) in the charge transport layer permits achievement of both the abrasion resistance and the electric characteristics of the photosensitive member. The reason for the above is thought to be as follows.

The resin (2) is easily dissolved in a solvent for forming a charge transport layer. As described above, the compound (1) also has excellent solubility in a solvent, and thus the combined use of the compound (1) and the resin (2) makes it easier to prepare an application liquid for charge transport layer formation in which the compound (1) and the resin (2) are uniformly dispersed. This is consequently thought to form a photosensitive layer in which the compound (1) and the resin (2) are uniformly dispersed. The compound (1) and the resin (2) tend to have excellent compatibility therebetween. Also in this point, this is consequently through to form a photosensitive layer in which the compound (1) and the resin (2) are uniformly dispersed. As a result of forming the photosensitive layer in which the compound (1) and the resin (2) are uniformly dispersed, the electric characteristics of the photosensitive member are thought to improve. Further, the compound (1) and the resin (2) easily form a stacking structure in the charge transport layer. Thus, layer density of the charge transport layer is thought to improve, which improves strength of the charge transport layer. As a result, the abrasion resistance of the photosensitive member is thought to improve. Even when the photosensitive member is a single-layer type photosensitive member, containing the compound (1) and the resin (2) in the single-layer type photosensitive layer is thought to achieve both the abrasion resistance and the electric characteristics of the photosensitive member. The reason for the above is the same as that in case of the multi-layer type photosensitive member.

The alkyl group represented by $R_{21}$, $R_{22}$, $R_{23}$, and $R_{24}$ in the general formula (2) is preferably an alkyl group having a carbon number of at least 1 and no greater than 4 and more preferably a methyl group or an ethyl group.

The aryl group represented by $R_{21}$, $R_{22}$, $R_{23}$, and $R_{24}$ in the general formula (2) is, for example, an aryl group having a carbon number of at least 6 and no greater than 14.

The cycloalkylidene group formed by bonding the $R_{23}$ and $R_{24}$ to each other in the general formula (2) is, for example, a cycloalkylidene group having a carbon number of at least 5 and no greater than 7. Examples of the cycloalkylidene group having a carbon number of at least 5 and no greater than 7 include a cyclopentylidene group, a cyclohexylidene group, and a cycloheptylidyne group. The cycloalkylidene group formed by bonding $R_{23}$ and $R_{24}$ to each other is preferably the cyclohexylidene group.

To achieve both the abrasion resistance and the electric characteristics of the photosensitive member, $R_{21}$ and $R_{22}$ in the general formula (2) each represent, independently from each other, preferably a hydrogen atom or an alkyl group having a carbon number of at least 1 and no greater than 4 and more preferably represent a hydrogen atom or a methyl group.

To achieve both the abrasion resistance and the electric characteristics of the photosensitive member, $R_{23}$ and $R_{24}$ in the general formula (2) each represent, independently from each other, preferably a hydrogen atom or an alkyl group having a carbon number of at least 1 and no greater than 4. For the same reason, $R_{23}$ and $R_{24}$ preferably bond to each other to represent a cycloalkylidene group having a carbon number of at least 5 and no greater than 7.

To further improve the abrasion resistance and the electric characteristics of the photosensitive member, $R_{23}$ and $R_{24}$ in the general formula (2) each represent, independently from each other, preferably an alkyl group having a carbon number of at least 1 and no greater than 4. For the same reason, $R_{23}$ more preferably represents an ethyl group and $R_{24}$ more preferably represents a methyl group.

To further improve the abrasion resistance and the electric characteristics of the photosensitive member, $R_{23}$ and $R_{24}$ in the general formula (2) preferably also bond to each other to represent a cycloalkylidene group having a carbon number of at least 5 and no greater than 7. For the same reason, $R_{23}$ and $R_{24}$ more preferably bond to each other to represent a cyclohexylidene group.

As the resin (2), a resin having a repeating unit represented by chemical formulae (Resin-1) to (Resin-4) is provided.

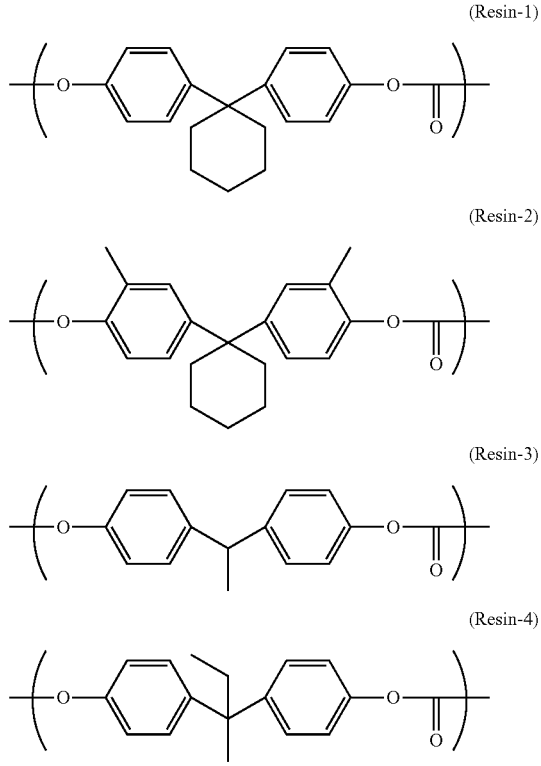

(Resin-1)

(Resin-2)

(Resin-3)

(Resin-4)

The resin (2) has a viscosity average molecular weight of preferably at least 40,000 and more preferably at least 40,000 and no greater than 52,500. When the viscosity average molecular weight of the resin (2) is at least 40,000, the abrasion resistance of the resin (2) can sufficiently be improved, making it difficult for the charge transport layer to abrade away. On the other hand, when the viscosity average molecular weight of the resin (2) is no greater than 52,500, upon formation of the charge transport layer, the resin (2) is easily dissolved in the solvent, which tends to make it easy to form the charge transport layer.

No limitations are placed on a method for producing a binder resin so long as the method can produce the resin (2). As one example of the method for producing the resin (2), a method (so-called a phosgene method) for performing condensed polymerization of a diol compound and phosgene forming a repeating unit of a polycarbonate resin is provided. More specifically, for example, a method for performing condensed polymerization of a diol compound represented by general formula (2-1) and phosgene is provided. $R_{21}$, $R_{22}$, $R_{23}$, and $R_{24}$ in the general formula (2-1) are respectively equivalent to $R_{21}$, $R_{22}$, $R_{23}$, and $R_{24}$ in the general formula (2). As another example of the method for producing the resin (2), a method for causing an ester exchange reaction between a diol compound and diphenyl carbonate is provided.

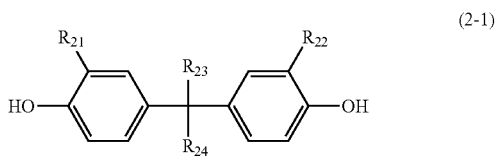

(2-1)

A number ratio of the repeating unit represented by the general formula (2) is preferably at least 80% by number, more preferably at least 90% by number, and even more preferably 100% by number relative to a total number of repeating units in the resin (2). The resin (2) may include any one of the repeating units represented by the (2) or may include a combination of any two or more types of the repeating units represented by the general formula (2).

The charge transport layer may contain the resin (2) alone as the binder resin. Alternatively, the charge transport layer may further contain, in addition to the resin (2), another binder resin other than the resin (2). Examples of another binder resin include a thermoplastic resin other than the resin (2), a thermosetting resin, and a photocurable resin. Examples of the thermoplastic resin include a polyarylate resin, a styrene-butadiene copolymer, a styrene-acrylonitrile copolymer, a styrene-maleate copolymer, an acrylic acid polymer, a styrene-acrylate copolymer, a polyethylene resin, an ethylene-vinyl acetate copolymer, a chlorinated polyethylene resin, a polyvinyl chloride resin, a polypropylene resin, an ionomer resin, a vinyl chloride-vinyl acetate copolymer, an alkyd resin, a polyamide resin, an urethane resin, a polysulfone resin, a diallyl phthalate resin, a ketone resin, a polyvinyl butyral resin, a polyester resin, and a polyether resin. Examples of the thermosetting resin include a silicone resin, an epoxy resin, a phenolic resin, a urea resin, and a melamine resin. Examples of the photocurable resin include an epoxy acrylate (an acrylic acid adduct of an epoxy compound) and a urethane acrylate (an acrylic acid adduct of a urethane compound). Any one of the binder resins may be used alone or a combination of any two or more types of the binder resins may be used.

A content amount of the resin (2) is preferably at least 80% by mass, more preferably at least 90% by mass, and even more preferably 100% by mass relative to a total mass of the binder resin contained in the charge transport layer.

The binder resin has a viscosity average molecular weight of preferably at least 40,000 and more preferably at least 40,000 and no greater than 52,500. When the viscosity average molecular weight of the binder resin is at least 40,000, the abrasion resistance of the photosensitive member easily improves. When the viscosity average molecular weight of the binder resin is no greater than 52,500, the binder resin is easily dissolved in the solvent upon formation of the photosensitive layer, and viscosity of the application liquid for a charge transport layer or the application liquid for a single-layer type photosensitive layer does not become too high. As a result, the charge transport layer or the single-layer type photosensitive layer is easily formed.

<8. Base Resin>

When the photosensitive member is a multi-layer type photosensitive member, the charge generating layer contains a base resin. No limitations are placed on the base resin so long as the base resin can be applied to the photosensitive member. Examples of the base resin include a thermoplastic resin, a thermosetting resin, and a photocurable resin. Examples of the thermoplastic resin include a styrene-butadiene copolymer, a styrene-acrylonitrile copolymer, a styrene-maleate copolymer, a styrene-acrylate copolymer, an acrylic acid polymer, a polyethylene resin, an ethylene-vinyl acetate copolymer, a chlorinated polyethylene resin, a polyvinyl chloride resin, a polypropylene resin, an ionomer, a vinyl chloride-vinyl acetate copolymer, an alkyd resin, a polyamide resin, an urethane resin, a polycarbonate resin, a polyarylate resin, a polysulfone resin, a diallyl phthalate resin, a ketone resin, a polyvinyl butyral resin, a polyether resin, and a polyester resin. Examples of the thermosetting resin include a silicone resin, an epoxy resin, a phenolic resin, a urea resin, a melamine resin, and other cross linkable thermosetting resins. Examples of the photocurable resin include an epoxy acrylate (an acrylic acid adduct of an epoxy compound) and a urethane acrylate (an acrylic acid adduct of a urethane compound). Any one of the base resins may be used alone or a combination of two or more types of the binder resins may be used.

The base resin contained in the charge generating layer is preferably different from the binder resin contained in the charge transport layer. In production of the multi-layer type photosensitive member, for example, the charge generating layer is formed on the conductive substrate and the charge transport layer is formed on the charge generating layer. At this point, an application liquid for a charge transport layer is applied onto the charge generating layer. Thus, the charge generating layer is preferably not dissolved in a solvent of the application liquid for a charge transport layer.

<9. Additives>

The photosensitive layer (the charge generating layer, the charge transport layer, or the single-layer type photosensitive member) of the photosensitive member may include any of various types of additives when necessary. Examples of the additives include antidegradants (for example, an antioxidant, a radical scavenger, a singlet quencher, and an ultraviolet absorbing agent), a softener, a surface modifier, an extender, a thickener, a dispersion stabilizer, a wax, an acceptor, a donor, a surfactant, a plasticizer, a sensitizer, and a leveling agent. Examples of the antioxidant include hindered phenol (for example, di(tert-butyl)p-cresol), hindered amine, paraphenylenediamine, arylalkane, hydroquinon, spirochromane, spiroindanone, and derivatives of those just mentioned, an organosulfur compound, and an organophosphorous compound.

<10. Intermediate Layer>

The intermediate layer (underlying layer) contains, for example, inorganic particles and a resin used for an intermediate layer (intermediate layer resin). Under the presence of the intermediate layer, it is thought that while maintaining an insulating state to such a degree that can suppress occurrence of leakage, a flow of current generated upon exposure of the photosensitive member is smoothened, thus suppressing a resistance increase.

Examples of the inorganic particles include particles of metals (for example, aluminum, iron, and coper), metal oxides (for example, a titanium oxide, alumina, a zirconium oxide, a tin oxide, and a zinc oxide) and particles of non-metal oxides (for example, silica). Any one type of the inorganic particles may be used alone or a combination of any two or more types of the inorganic particles may be used.

No limitations are placed on the intermediate layer resin so long as the intermediate layer resin can be used as a resin forming an intermediate layer. The intermediate layer may include any of various types of additives. Examples of the additives are the same as those included in the photosensitive layer.

<11. Method for Producing Photosensitive Member>

When the photosensitive member is a multi-layer type photosensitive member, the multi-layer type photosensitive member is produced, for example, in a manner described below. The method for producing the multi-layer type photosensitive member includes, for example, a charge transport layer formation process. The method for producing the multi-layer type photosensitive member may further include a charge generating layer formation process. The method for producing the multi-layer type photosensitive member may be carried with some appropriate alteration when necessary.

In the charge generating layer formation process, the application liquid for charge generating layer formation containing at least a charge generating material and a solvent is applied onto the conductive substrate. Then at least part of the solvent included in the application liquid for charge generating layer formation is removed to form a charge generating layer on the conductive substrate. The application liquid for charge generating layer formation is prepared by dissolving or dispersing, in the solvent, the charge generating material and any component (for example, a base resin and any of various types of additives) added when necessary.

In the charge transport layer formation process, an application liquid for charge transport layer formation containing at least a hole transport material, a binder resin, and a solvent is applied onto the charge generating layer. Then at least part of the solvent is removed to form a charge transport layer. Consequently, a multi-layer type photosensitive member is produced. The application liquid for charge transport layer formation is prepared by dissolving or dispersing, in the solvent, a hole transport material, a binder resin, and any component (for example, an electron acceptor compound and any of various types of additives) added when necessary. The hole transport material is the compound (1). A preferable example of the binder resin is the resin (2).

Next, when the photosensitive member is a single-layer type photosensitive member, the single-layer type photosensitive member is produced, for example, in a manner described below. The single-layer type photosensitive member is produced by applying an application liquid for a single-layer type photosensitive layer onto the conductive substrate and drying them. The application liquid for a single-layer type photosensitive layer is produced by dissolving or dispersing, in a solvent, the hole transport material and any component (for example, a charge generating material, an electron transport material, a binder resin, and any of various types of additives) added when necessary.

No limitations are placed on the solvent contained in the application liquid (the application liquid for a charge generating layer, the application liquid for a charge transport layer, or the application liquid for a single-layer type photosensitive layer) so long as each of components included in the application liquid can be dissolved or dispersed in the solvent. Examples of the solvent include alcohols (for example, methanol, ethanol, isopropanol, and butanol), aliphatic hydrocarbons (for example, n-hexane, octane, and cyclohexane), aromatic hydrocarbons (for example, benzene, toluene, and xylene), halogenated hydrocarbon (for example, dichloromethane, dichloroethane, carbon tetrachloride, and chlorobenzene), ethers (for example, dioxane, dimethyl ether, diethyl ether, tetrahydrofuran, ethylene glycol dimethyl ether, diethylene glycol dimethyl ether, and propylene glycol monomethyl ether), ketones (for example, acetone, methyl ethyl ketone, and cyclohexanone), esters (for example, ethyl acetate and methyl acetate), dimethyl formaldehyde, dimethyl formamide, and dimethyl sulfoxide. Any one of the solvents may be used alone or a combination of any two or more types of the solvents may be used. As the solvent, a non-halogen solvent (a solvent other than that of halogenated hydrocarbon) is preferably used to improve workability upon the production of photosensitive members.

The solvent contained in the application liquid for charge transport layer formation preferably contains at least one type of toluene, dioxane (for example, 1,4-dioxane), tetrahydrofuran, and xylene (for example, ortho-xylene (o-xylene)). The compound (1) as the hole transport material and the resin (2) as the binder resin tend to be favorably dispersed in such solvents. Thus, the application liquid for charge transport layer formation in which the compound (1) and the resin (2) are uniformly dispersed is easily prepared. Forming a charge transport layer using such an application liquid for charge transport layer formation makes it easy to form a charge transport layer in which the compound (1) is uniformly dispersed. As a result of forming the charge transport layer using such an application liquid for charge transport layer formation, the charge transport layer is easily formed in which the compound (1) is uniformly dispersed. The solvent contained in the application liquid for charge transport layer formation more preferably contains one or two types of toluene, 1,4-dioxane, tetrahydrofuran, and o-xylene. When the solvent contained in the application liquid for charge transport layer formation contains two types of toluene, 1,4-dioxane, tetrahydrofuran, and o-xylene, examples of such a solvent include a mixed solvent of tetrahydrofuran and toluene, a mixed solvent of tetrahydrofuran and 1-4-dioxane, and a mixed solvent of tetrahydrofuran and o-xylene.

The solvent contained in the application liquid for charge transport layer formation is preferably different from the solvent contained in the application liquid for charge generating layer formation. Upon application of the application liquid for charge transport layer formation onto the charge generating layer, the charge generating layer is preferably not dissolved in the application liquid for charge transport layer formation.

The application liquid is prepared by mixing the different components and dispersing the components in the solvent. For the mixture or dispersion, for example, a bead mill, a roll mill, a ball mill, an attritor, a paint shaker, or an ultrasonic disperser can be used.

The application liquid (the application liquid for a charge generating layer, the application liquid for a charge transport layer, or the application liquid for a single-layer type photosensitive layer) may contain, for example, a surfactant to improve dispensability of each component.

No limitations are placed on a method for applying the application liquid (the application liquid for a charge generating layer, the application liquid for a charge transport layer, or the application liquid for a single-layer type photosensitive layer) so long as the method can achieve uniform application of the application liquid onto the conductive substrate. Examples of the application method include dip coating, spray coating, spin coating, and bar coating.

No limitations are placed on a method for removing at least part of the solvent contained in the application liquid (the application liquid for charge generating layer formation, the application liquid for charge transport layer formation, or the application liquid for a single-layer type photosensitive layer) so long as the method can evaporate the solvent in the application liquid. Examples of the method for removing at least part of the solvent include heating, depressurization, and a combination of heating and depressurization. For example, a method for thermal treatment (hot-air drying) using a high-temperature dryer or a reduced pressure dryer is provided. Thermal treatment condition is, for example, a temperature of at least 40° C. and no greater than 150° C. and for at least three minutes and no greater than 120 minutes.

Note that the method for producing the photosensitive member may further include one or both of a process of forming an intermediate layer and a process of forming a protective layer when necessary. In the process of forming an intermediate layer and the process of forming a protective layer, a well-known method is appropriately selected.

The photosensitive member and the method for producing the photosensitive member according to the present embodiment have been described above. With the photosensitive member of the present embodiment, the electric characteristics of the photosensitive member can be improved. With the photosensitive member of the present embodiment, both the abrasion resistance and the electric characteristics can be improved. With the method for producing the photosensitive member of the present embodiment, a photosensitive member can be produced which achieves both the abrasion resistance and the electric characteristics.

EXAMPLES

The present disclosure will be described in more detail, referring to examples. Note that, however, the present disclosure is not in any way limited by the following embodiments.

<Material of Photosensitive Member>

As materials for forming the charge generating layer and the charge transport layer of the multi-layer type photosensitive member, a hole transport material and a charge generating material below were prepared. As materials for forming the single-layer type photosensitive layer of the single-layer type photosensitive member, a hole transport material, a charge generating material, and an electron transport material below were prepared.

<Hole Transport Material>

As the hole transport material, the compounds (H-1) to (H-6) described in the first embodiment were used. The compounds (H-1) to (H-6) were produced in respective methods described below.

(Production of Compound (3a))

First, a compound (3a) was produced in accordance with reaction (R-4). The compound (3a) is a raw material for producing compounds (5a), (5b), and (5c) described below.

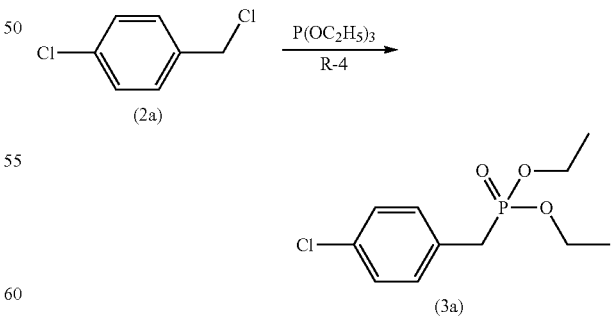

In the reaction (R-4), a compound (2a) and triethyl phosphite were reacted to each other to obtain the compound (3a). More specifically, 16.1 g (0.10 moles) of the compound (2a) and 25.0 g (0.15 moles) of triethyl phosphite were introduced into a flask having a capacity of 200 mL.

Contents of the flask were stirred at 180° C. for eight hours and then cooled down to room temperature. Subsequently, the non-reacted triethyl phosphite contained in the contents of the flask was subjected to reduced pressure distillation to be removed. Consequently, the compound (3a) as a white liquid was obtained (with a yield amount of 24.1 g and a yield ratio of 92 mole %).

(Production of Compounds (5a), (5b) and (5c))

First, the compound (5a) was produced in accordance with reaction (R-5).

The compound (5a) is a raw material for producing the compounds (H-1), (H-2), and (H-4) described below.

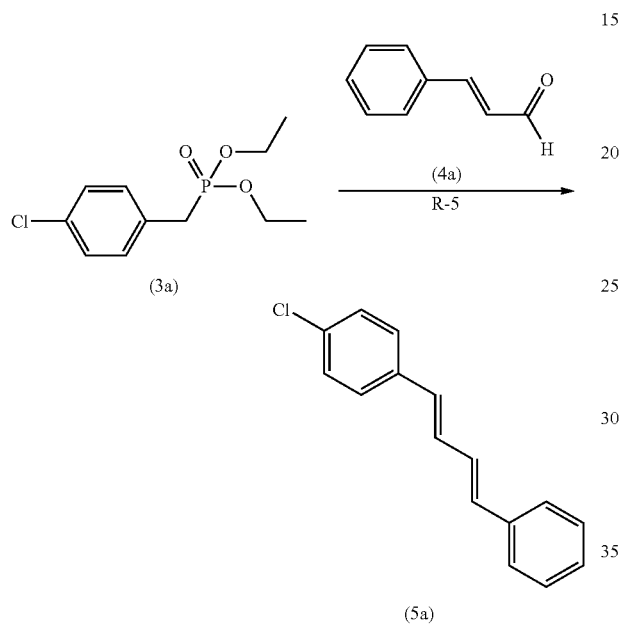

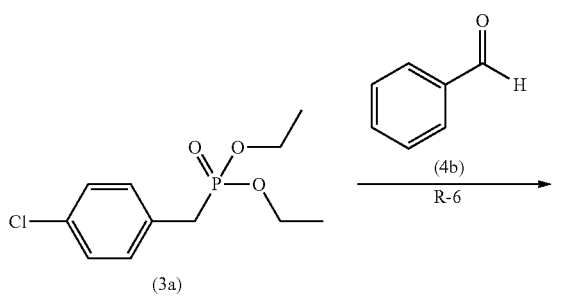

In the reaction (R-5), the compound (3a) and the compound (4a) were reacted to each other to obtain the compound (5a). The reaction (R-5) is Wittig reaction. More specifically, 13.1 g (0.050 moles) of the compound (3) obtained in the reaction (R-4) was added at 0° C. to a two-necked flask having a capacity of 500 mL. The air in the flask was replaced with argon gas. Subsequently, 100 mL of dry tetrahydrofuran and 9.3 g (0.050 moles) of 28% sodium methoxide were added into the flask. Contents of the flask were stirred for 30 minutes. Subsequently, a solution containing 6.6 g (0.050 moles) of the compound (4a) and 300 mL of dry tetrahydrofuran were added into the flask. Contents of the flask were stirred at room temperature for 12 hours. The contents of the flask were poured into ion exchanged water and extracted with toluene. An obtained organic layer was washed with the ion exchanged water five times and dried using anhydrous sodium sulfate. Subsequently, a solvent contained in the organic layer was distilled to obtain residue. The obtained residue was purified using a mixture of 20 mL of toluene and 100 mL of methanol. Consequently, the compound (5a) as a white crystal was obtained. A yield amount of the compound (5a) was 10.8 g, and a yield ratio of the compound (5a) from the compound (3a) was 90 mol %.

The compound (5b) was produced in accordance with reaction (R-6). The compound (5b) is a raw material for producing the compounds (H-3) and (H-5) described below.

In the reaction (R-6), the compound (3a) and the compound (4a) were reacted to each other to obtain the compound (5b). The reaction (R-6) is Wittig reaction. The reaction (R-6) was performed with the same method as that used for the reaction (R-5) in points other than the following points. Alteration from 6.6 g (0.050 moles) of the compound (4a) in the reaction (R-5) into 5.0 g (0.050 moles) of the compound (4b) was made. As a result, the compound (5b) was obtained. A yield amount of the compound (5b) was 9.9 g and a yield ratio of the compound (5b) from the compound (3a) was 92 mol %.

The compound (5c) was produced in accordance with reaction (R-7). The compound (5c) is a raw material for producing the compound (H-6) described below.

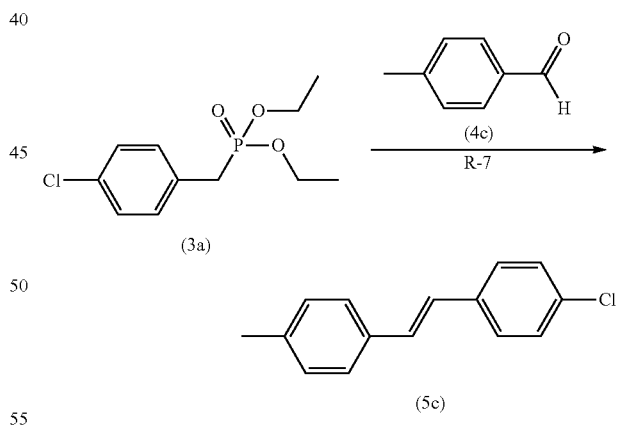

In the reaction (R-7), the compound (3a) and the compound (4c) were reacted to each other to obtain the compound (5c). The reaction (R-7) is Wittig reaction. The reaction (R-7) was performed in the same method as that used for the reaction (R-5) in points other than the following points. Alteration from 6.6 g (0.050 moles) of the compound (4a) in the reaction (R-5) to 6.0 g (0.050 moles) of the compound (4c) was made. As a result, the compound (5c) was obtained. A yield amount of the compound (5c) is 10.5 g, and a yield ratio of the compound (5c) from the compound (3a) is 92 mol %.

(Production of Compound (H-1))

First, the compound (H-1) was produced in accordance with the reaction (R-8).

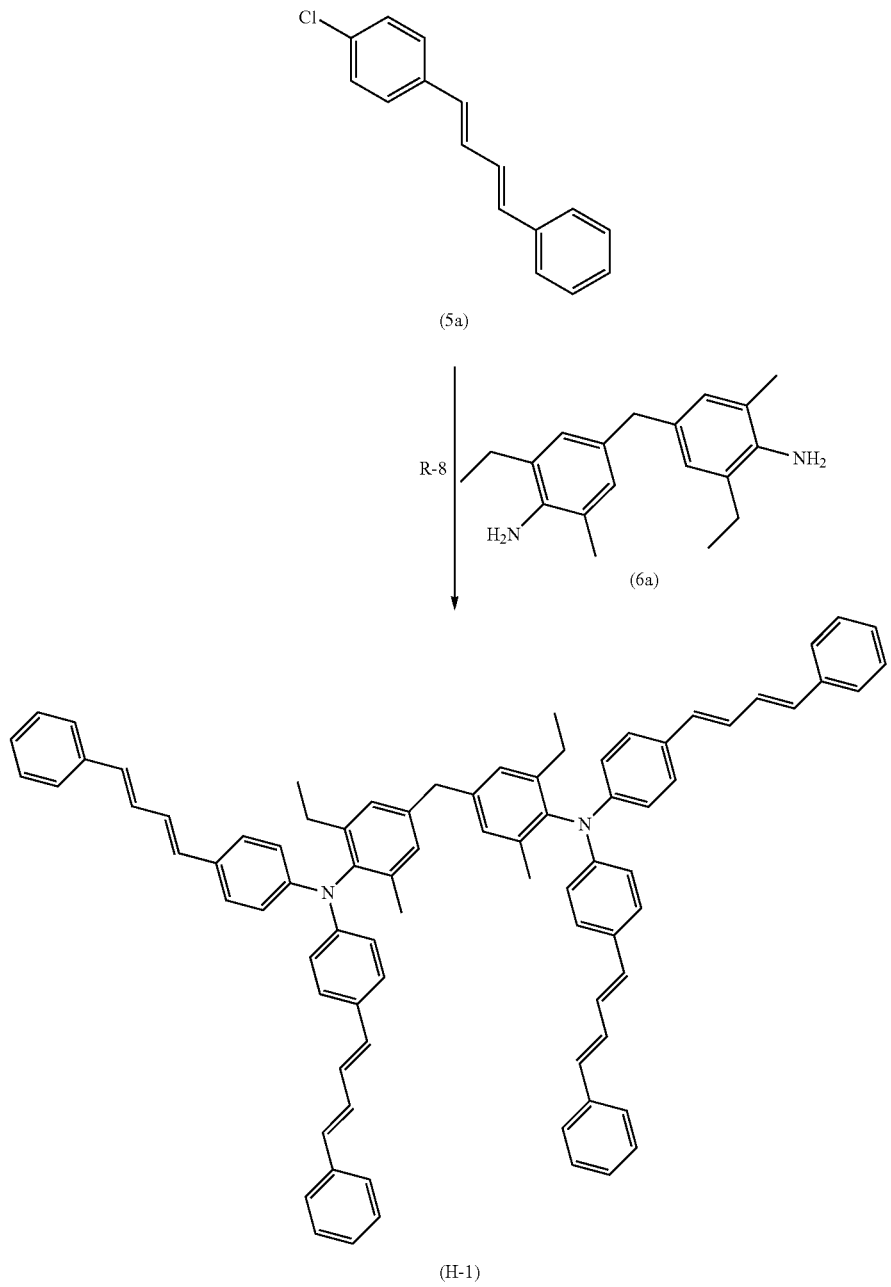

In the reaction (R-8), the compound (5a) and the compound (6a) were reacted to each other to obtain the compound (H-1). The reaction (R-8) is coupling reaction. More specifically, 9.62 g (0.040 moles) of the compound (5a) as a first raw material, 0.140 g (0.0004 moles) of tricyclohexylphosphine, 0.091 g ($9.99 \times 10^{-5}$ moles) of tris (dibenzylideneacetone) dipalladium (0), 4.22 g (0.044 moles) of sodium tert-butoxide, 2.82 g (0.010 moles) of the compound (6a) as a second raw material, and 100 mL of distilled o-xylene were introduced into a three-necked flask. The air in the flask was replaced with argon gas. Subsequently, contents of the flask were stirred at 120° C. for five hours and then cooled down to room temperature. The contents of the flask were washed with ion exchanged water three times to obtain an organic layer. Anhydrous sodium sulfate and activated clay were added to the organic layer and drying treatment and adsorption treatment were performed. The organic layer already subjected to the drying treatment and the absorption treatment was subjected to reduced pressure distillation to remove the o-xylene. Consequently, a residue was obtained. The obtained residue was purified through silica gel column chromatography using chloroform and hexane (with a volume ratio of 1 to 1) as a developing solvent. Consequently, the compound (H-1) was obtained. A yield amount of the compound (H-1) was 5.7 g and a yield ratio of the compound (H-1) from the compound (6a) was 52 mol %.

(Production of Compounds (H-2) to (H-6))

The compounds (H-2) to (H-6) were each produced by the same method as that used for producing the compound (H-1) in points other than the following points. Note that raw materials respectively used in the production of the compounds (H-2) to (H-6) were added with the same number of moles as those of the corresponding raw materials used in the production of the compound (H-1).

The first raw material used in the reaction (R-8) was altered from the compound (5a) in the production of the compound (H-1) to the first raw material (the compound (5a), (5b), or (5c)) illustrated in Table 1. The second raw material used in the reaction (R-8) was altered from the compound (6a) in the production of the compound (H-1) to the second raw material (the compound (6a), (6b), (6c), or (6d)) illustrated in Table 1. As a result, in the reaction (R-8), the compounds (H-2) to (H-6) instead of the compound (H-1) were obtained. Table 1 illustrates yield amounts of the compounds (H-2) to (H-6) obtained in the reaction (R-8). Table 1 also illustrates yield ratios of the compounds (H-2) to (H-6) from the second raw material (the compound (6a), (6b), (6c), or (6d)).

In Table 1, the compounds (5a) to (5c) and (6a) to (6d) are each represented by Chemical Formulae (5a) to (5c) and (6a) to (6d). In Table 1, the compounds (5a) to (5c) are respectively compounds obtained in the (R-5) to (R-7) described above.

TABLE 1

| | Reaction (R-8) | | | | | | | |
|---|---|---|---|---|---|---|---|---|
| First raw material | | | Second raw material | | | Reaction product | | |
| Compound | Additive amount [g] | Additive amount [mol] | Compound | Additive amount [g] | Additive amount [mol] | Compound | Yield amount [g] | Yield ratio [mol %] |
| 5a | 9.62 | 0.040 | 6a | 2.82 | 0.010 | H-1 | 5.70 | 52 |
| 5a | 9.62 | 0.040 | 6b | 2.26 | 0.010 | H-2 | 5.53 | 53 |
| 5b | 8.58 | 0.040 | 6a | 2.82 | 0.010 | H-3 | 5.57 | 56 |
| 5a | 9.62 | 0.040 | 6c | 2.56 | 0.010 | H-4 | 5.37 | 50 |
| 5b | 8.58 | 0.040 | 6d | 3.10 | 0.010 | H-5 | 5.63 | 55 |
| 5c | 9.14 | 0.040 | 6a | 2.82 | 0.010 | H-6 | 5.57 | 53 |

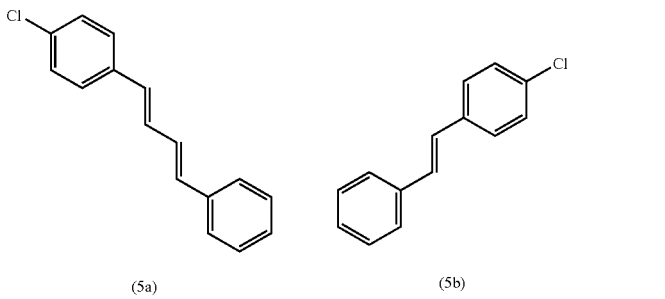 [SMILES: Clc1ccc(/C=C/C=C/c2ccccc2)cc1 ; Clc1ccc(/C=C/c2ccccc2)cc1]

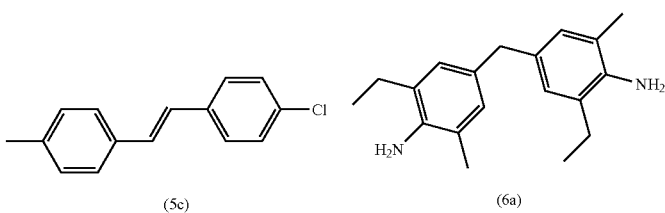

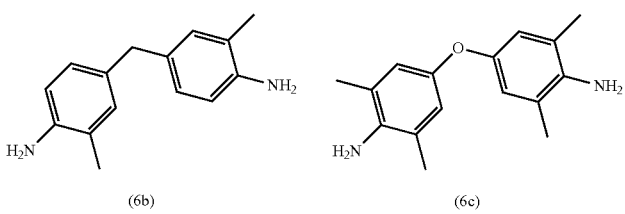 [SMILES: Cc1cc(Cc2ccc(N)c(C)c2)ccc1N ; Cc1cc(Oc2cc(C)c(N)c(C)c2)cc(C)c1N]

TABLE 1-continued

| Reaction (R-8) | | | | | | | | |
|---|---|---|---|---|---|---|---|---|
| First raw material | | | Second raw material | | | Reaction product | | |
| Compound | Additive amount [g] | Additive amount [mol] | Compound | Additive amount [g] | Additive amount [mol] | Compound | Yield amount [g] | Yield ratio [mol %] |

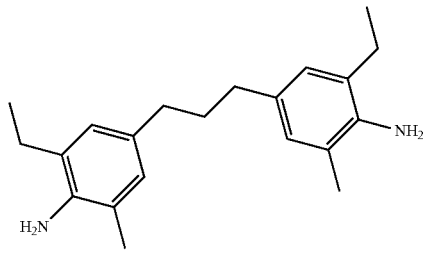

(6d)

Next, the produced compound (H-1) was analyzed using ¹H-NMR (a proton nuclear magnetic resonance spectrometer). Magnetic field intensity was set at 300 MHz. Deuterated chloroform (CDCl₃) was used as a solvent. Tetramethylsilane (TMS) was used as an internal standard substance. FIG. 1 illustrates a ¹H-NMR spectrum of the measured compound (H-1). Chemical shift values of the ¹H-NMR spectrum of the compound (H-1) are illustrated below. It was confirmed based on the ¹H-NMR spectrum and the chemical shift values that each compound (H-1) has a chemical structure represented by Chemical Formula (H-1).

Compound (H-1): ¹H-NMR (300 MHz, CDCl₃) δ 7.16-7.44 (m, 28H), 6.76-7.04 (m, 20H), 6.57-6.63 (m, 8H), 3.98 (s, 2H), 2.42 (q, 4H), 2.03 (s, 6H), 1.00 (t, 6H).

(Preparation of Compounds (H-A) and (H-B))

Compounds represented by Chemical Formulae (H-A) and (H-B) below were also prepared as hole transport materials. Hereinafter, the compounds represented by Chemical Formulae (H-A) and (H-B) may be referred to as compounds (H-A) and (H-B), respectively.

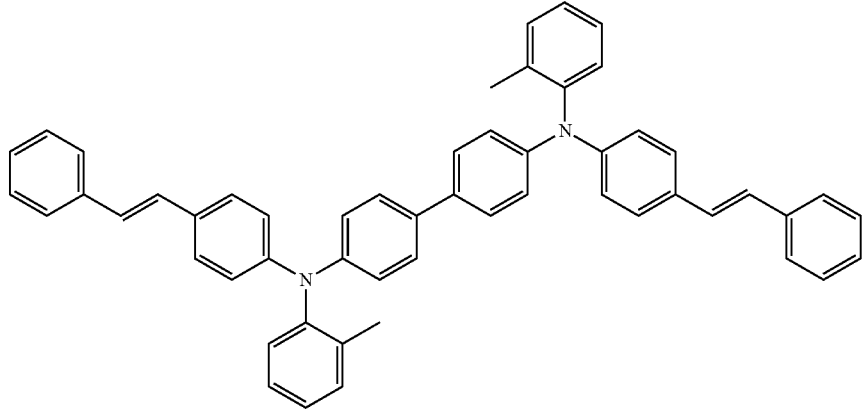

(H-A)

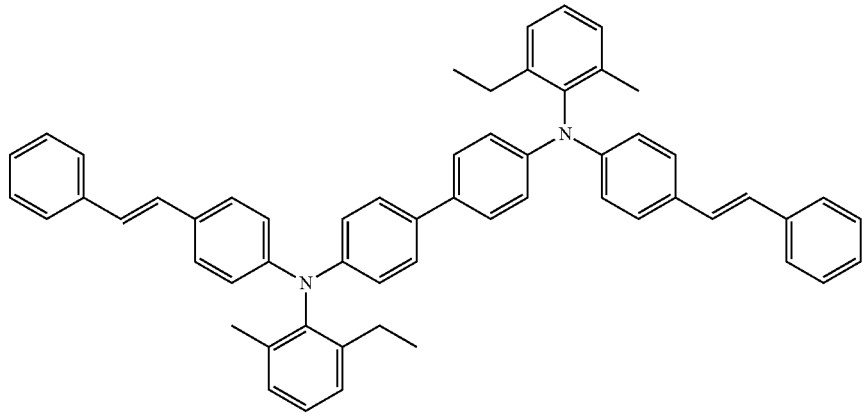

(H-B)

<5. Charge Generating Material>

Compounds (C-1X) and (C-2Y) were prepared as charge generating materials. The compound (C-1X) was metal-free phthalocyanine represented by Chemical Formula (C-1) described in the second embodiment. The compound (C-1X) had an X-type crystal structure.

The compound (C-2Y) was titanyl phthalocyanine represented by Chemical Formula (C-2) described in the second embodiment. The compound (C-2Y) had a Y-type crystal structure. The compound (C-2Y) had a main peak at 27.2° with a Bragg angle of 2θ±0.2° in a CuKα characteristic X-ray diffraction spectrum.

(Electron Transport Material)

The compounds (E-1) and (E-2) described in the second embodiment were prepared as the electron transport materials contained in the single-layer type photosensitive layer of the single-layer type photosensitive member.

(Binder Resin)

As the binder resin, a bisphenol Z polycarbonate resin ("Panlite" (registered Japanese trademark) TS-2050" produced by TEIJIN Limited, with a viscosity average molecular weight of 50,000) was prepared. In addition, as the binder resin, resins (Resin-1a) to (Resin-5a) were prepared.

The resin (Resin-1a) was a resin that has, as a repeating unit, only a repeating unit represented by Chemical Formula (Resin-1) described in the second embodiment. The resin (Resin-1a) had a viscosity average molecular weight of 45,000.

The resin (Resin-2a) was a resin that has, as a repeating unit, only a repeating unit represented by Chemical Formula (Resin-2) described in the second embodiment. The resin (Resin-2a) had a viscosity average molecular weight of 51,100.

The resin (Resin-3a) was a resin having, as a repeating unit, only a repeating unit represented by Chemical Formula (Resin-3) described in the second embodiment. The resin (Resin-3a) had a viscosity average molecular weight of 47,600.

The resin (Resin-4a) was a resin that has, as a repeating unit, only a repeating unit represented by Chemical Formula (Resin-4) described in the second embodiment. The resin (Resin-4a) had a viscosity average molecular weight of 48,800.

The resin (Resin-5a) was a polyarylate resin that has, as a repeating unit, only a repeating unit represented by Chemical Formula (Resin-5) below. The resin (Resin-5a) had a viscosity average molecular weight of 50,500.

size of 10 nm) subjected to surface treatment was prepared. More specifically, the titanium oxide was subjected to surface treatment with alumina and silica, and while subjecting the surface-treated titanium oxide to wet dispersion, the surface-treated titanium oxide was further subjected to surface treatment using methyl hydrogen polysiloxane.

Next, an application liquid for an undercoat layer was prepared. More specifically, 2.8 parts by mass of the titanium oxide subjected to surface treatment, 1 part by mass of a copolymer polyamide resin ("DAIAMID X 4685" produced by Daicel Evonik Ltd., 10 parts by mass of ethanol as a solvent, and 2 parts by mass of butanol as a solvent were introduced into a container. Contents of the container were mixed with a bead mill for five hours, and the materials were dispersed in the solvent. Consequently, an application liquid for an undercoat layer was obtained.

Next, an undercoat layer was formed. More specifically, the obtained application liquid for an undercoat layer was filtered with a 5 m-sized filter. Then the application liquid for an undercoat layer was applied by dip coating to a surface of a drum-shaped support body (with a diameter of 30 mm and a total length of 238.5 mm) of aluminium as a conductive substrate. Subsequently, the applied application liquid for an undercoat layer was heated at 130° C. for thirty minutes. Consequently, an undercoat layer (with a film thickness of 1.5 μm) was formed on the conductive substrate.

Next, an application liquid for a charge generating layer was prepared. More specifically, 1 part by mass of a compound (C-2Y) as a charge generating material and 1 part by mass of a polyvinyl butyral resin as a base resin ("Denka butyral #6000EP" produced by Denka Co., Ltd.), 40 parts by mass of propylene glycol monomethyl ether as a dispersion medium, and 40 parts by mass of tetrahydrofuran as a dispersion medium were introduced into a container. Contents of the container were mixed with a bead mill for two hours, and the material was dispersed in the dispersion medium. Consequently, an application liquid for a charge generating layer was obtained. Next, the obtained application liquid for a charge generating layer was filtered with a 3 m-sized filter. Then the application liquid for a charge generating layer was applied to the formed undercoat layer by dip coating. Subsequently, the applied application liquid for a charge generating layer was dried at 50° C. for five minutes. Consequently, a charge generating layer (with a film thickness of 0.3 μm) was formed on the undercoat layer.

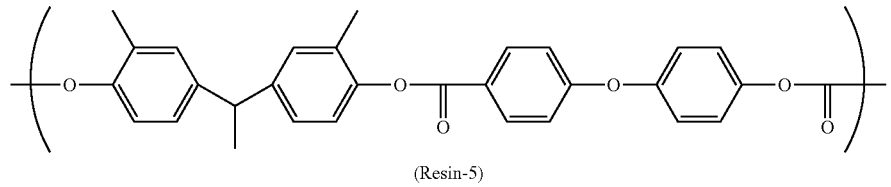

(Resin-5)

<Production of Multi-Layer Type Photosensitive Members (P-A1) to (P-A6) and (P-B1) to (P-B2)>

The aforementioned material for forming the photosensitive layer was used to produce multi-layer type photosensitive members (P-A1) to (P-A6) and (P-B1) to (P-B2).

(Production of Multi-Layer Type Photosensitive Member (P-A1)>

First, a titanium oxide ("Sample SMT-02" produced by TAYCA Corporation with a number average primary particle Next, an application liquid for a charge transport layer was prepared. More specifically, 70 parts by mass of the compound (H-1) as a hole transport material, 100 parts by mass of a bisphenol Z polycarbonate resin ("Panlite (registered Japanese trademark))TS-2050" with a viscosity average molecular weight of 50,000 produced by Teijin Limited) as a binder resin, 5 parts by mass of BHT (di(tert-butyl)p-cresol) as an additive, 430 parts by mass of tetrahydrofuran as a solvent, and 430 parts by mass of toluene as a solvent were introduced into a container. Contents of the container were mixed, and the materials were dissolved in the solvent. Consequently, the application liquid for a charge transport layer was obtained. Next, the obtained application liquid for a charge transport layer was applied onto the formed charge generating layer through the same method as that used for the application liquid for a charge generating layer. Subsequently, the applied application liquid for a charge transport layer was dried at 130° C. for 30 minutes. Consequently, a charge transport layer (with a film thickness of 20 μm) was formed on the charge generating layer. As a result, a multi-layer type photosensitive member (P-A1) was obtained.

<Production of Multi-layer type photosensitive members (P-A2) to (P-A6) and (P-B1) and (P-B2)>

The multi-layer type photosensitive members (P-A2) to (P-A6) and (P-B1) and (P-B2) were each produced by the same method as that used for producing the multi-layer type photosensitive member (P-A1), with a change made in the following point. The compound (H-1) serving as the hole transport material used for producing the multi-layer type photosensitive member (P-A1) was altered to a hole transport material of a type illustrated in Table 2.

<Production of Single-Layer Type Photosensitive Members (P-C1) to (P-C18) and (P-D1) to (P-D6)>

Single-layer type photosensitive members (P-C1) to (P-C18) and (P-D1) to (P-D6) were produced by using the material for the photosensitive member.

<Production of Single-Layer Type Photosensitive Member (P-C1)>

Five parts by mass of a compound (C-1X) serving as a charge generating material, 80 parts by mass of the compound (H-1) serving as the hole transport material, 40 parts by mass of the compound (E-2) as an electron transport material, 100 parts by mass of a bisphenol Z polycarbonate resin ("Panlite (registered Japanese trademark) TS-2050" produced by Teijin Limited with a viscosity average molecular weight of 50,000) serving as a binder resin, and 800 parts by mass of tetrahydrofuran serving as a solvent were introduced into a container. Contents of the container were mixed with a ball mill for 50 hours, and the materials were dispersed in the solvent. Consequently, the application liquid for a single-layer type photosensitive member was obtained. Then the application liquid for a single-layer type photosensitive member was applied by using dip coating to a drum-shaped support body (with a diameter of 30 mm and a full length of 238.5 mm) of aluminum serving as a conductive substrate. Subsequently, the applied application liquid for a single-layer type photosensitive member was dried with hot wind at 100° C. for 30 minutes. Consequently, a single-layer type photosensitive layer (with a film thickness of 25 μm) was formed on the conductive substrate. As a result, a single-layer type photosensitive member (P-C1) was obtained.

<Production of Single-Layer Type Photosensitive Members (P-C2) to (P-C18) and (P-D1) to (P-D6)>

The single-layer type photosensitive members (P-C2) to (P-C18) and (P-D1) to (P-D6) were each produced by the same method as that used for producing the single-layer type photosensitive member (P-C1) with a change made in the following points. A compound (C-1X) serving as a charge generating material used for producing the single-layer type photosensitive member (P-C1) was altered to a charge generating material of a type illustrated in Table 3. The compound (H-1) serving as the hole transport material used for producing the single-layer type photosensitive member (P-C1) was altered to a hole transport material of a type illustrated in Table 3. The compound (E-2) serving as the electron transport material used for producing the single-layer type photosensitive member (P-C1) was altered to an electron transport material of a type illustrated in Table 3.

<Evaluation of Electric Characteristics of Multi-Layer Type Photosensitive Members (P-A1) to (P-A6) and (P-B1) and (P-B2)>

The electric characteristics of the produced multi-layer type photosensitive members (P-A1) to (P-A6) and (P-B1) to (P-B2) were each evaluated. The evaluation of the electric characteristics was performed under environment with a temperature of 23° C. and a humidity of 60% RH (relative humidity). First, a surface of the multi-layer type photosensitive member was negatively charged using a drum sensitivity test device (produced by Gentech Corporation). As charge condition, a rotation speed of the multi-layer type photosensitive member was set at 31 rpm and a current flowing into the multi-layer type photosensitive member was set at −8 μA. Surface potential of the multi-layer type photosensitive member immediately after the charging thereof was measured. The measured surface potential of the multi-layer type photosensitive member was defined as an initial potential ($V_0$, unit of V). Next, monochromatic light (with a wavelength of 780 nm, a half-width of 20 nm, and an optical energy of 0.4 μJ/cm$^2$) was extracted from white light of a halogen lamp using a bandpass filter. The extracted monochromatic light was irradiated to the surface of the multi-layer type photosensitive member. The surface potential of the multi-layer type photosensitive member upon passage of 0.5 seconds after ending of the irradiation was measured. The measured surface potential was defined as a sensitivity potential ($V_L$, unit of V). Table 2 illustrates measured initial potential ($V_0$) and sensitivity potential ($V_L$) of the multi-layer type photosensitive member. Note that a smaller absolute value of the sensitivity potential ($V_L$) indicates more excellent electric characteristics of the multi-layer type photosensitive member.

<Evaluation of Electric Characteristics of Single-Layer Type Photosensitive Members (P-C1) to (P-C18) and (P-D1) to (P-D6)>

Electric characteristics of the produced single-layer type photosensitive members (P-C1) to (P-C18) and (P-D1) to (P-D6) were each evaluated. The evaluation of the electric characteristics was performed under environment with a temperature of 23° C. and a humidity of 60% RH (relative humidity). First, surfaces of the single-layer type photosensitive members were positively charged using a drum sensitivity test device (produced by Gentech Corporation). As charge condition, a rotation speed of the single-layer type photosensitive member was set at 31 rpm and a current flowing into the single-layer type photosensitive member was set at +8 μA. Surface potential of the single-layer type photosensitive member immediately after the charging thereof was measured. The measured surface potential of the single-layer type photosensitive member was defined as an initial potential ($V_0$, unit of V). Next, monochromatic light (with a wavelength of 780 nm, a half-width of 20 nm, and an optical energy of 1.5 μJ/cm$^2$) was extracted from white light of a halogen lamp by using a bandpass filter. The extracted monochromatic light was irradiated to a surface of the single-layer type photosensitive member. A surface potential of the single-layer type photosensitive member upon passage of 0.5 seconds after ending of the irradiation was measured. The measured surface potential was defied as a sensitivity potential '($V_L$, unit of V). Table 3 illustrates measured initial potential ($V_0$) and sensitivity potential ($V_L$) of the single-layer type photosensitive member. Note that a smaller absolute value of the sensitivity potential ($V_L$)

indicates more excellent electric characteristics of the single-layer type photosensitive member.

Table 2 illustrates results of the electric characteristics of the multi-layer type photosensitive members. Table 3 illustrates results of the electric characteristics of the single-layer type photosensitive members. In Tables 2 and 3, CGM, HTM, ETM, $V_0$, and $V_L$ respectively represent a charge generating material, a hole transport material, an electron transport material, the initial potential, and the sensitivity potential.

TABLE 2

| | Multi-layer type photosensitive member | HTM | Electric characteristics | |
|---|---|---|---|---|
| | | | $V_0$ (V) | $V_L$ (V) |
| Example 1 | P-A1 | H-1 | −700 | −91 |
| Example 2 | P-A2 | H-2 | −700 | −93 |
| Example 3 | P-A3 | H-3 | −700 | −103 |
| Example 4 | P-A4 | H-4 | −700 | −93 |
| Example 5 | P-A5 | H-5 | −700 | −102 |
| Example 6 | P-A6 | H-6 | −700 | −100 |
| Comparative Example 1 | P-B1 | H-A | −700 | −113 |
| Comparative Example 2 | P-B2 | H-B | −700 | −111 |

TABLE 3

| | Single-layer type photosensitive member | CGM | HTM | ETM | Electric characteristics | |
|---|---|---|---|---|---|---|
| | | | | | $V_0$ (V) | $V_L$ (V) |
| Example 7 | P-C1 | C-1X | H-1 | E-2 | +701 | +97 |
| Example 8 | P-C2 | C-1X | H-1 | E-1 | +700 | +95 |
| Example 9 | P-C3 | C-2Y | H-1 | E-1 | +700 | +91 |
| Example 10 | P-C4 | C-1X | H-2 | E-2 | +700 | +98 |
| Example 11 | P-C5 | C-1X | H-2 | E-1 | +699 | +96 |
| Example 12 | P-C6 | C-2Y | H-2 | E-1 | +700 | +93 |
| Example 13 | P-C7 | C-1X | H-3 | E-2 | +700 | +104 |
| Example 14 | P-C8 | C-1X | H-3 | E-1 | +699 | +103 |
| Example 15 | P-C9 | C-2Y | H-3 | E-1 | +700 | +100 |
| Example 16 | P-C10 | C-1X | H-4 | E-2 | +700 | +97 |
| Example 17 | P-C11 | C-1X | H-4 | E-1 | +699 | +96 |
| Example 18 | P-C12 | C-2Y | H-4 | E-1 | +700 | +92 |
| Example 19 | P-C13 | C-1X | H-5 | E-2 | +700 | +103 |
| Example 20 | P-C14 | C-1X | H-5 | E-1 | +699 | +101 |
| Example 21 | P-C15 | C-2Y | H-5 | E-1 | +700 | +100 |
| Example 22 | P-C16 | C-1X | H-6 | E-2 | +700 | +105 |
| Example 23 | P-C17 | C-1X | H-6 | E-1 | +699 | +103 |
| Example 24 | P-C18 | C-2Y | H-6 | E-1 | +700 | +101 |
| Comparative Example 3 | P-D1 | C-1X | H-A | E-2 | +699 | +115 |
| Comparative Example 4 | P-D2 | C-1X | H-A | E-1 | +701 | +112 |
| Comparative Example 5 | P-D3 | C-2Y | H-A | E-1 | +700 | +109 |
| Comparative Example 6 | P-D4 | C-1X | H-B | E-2 | +700 | +113 |
| Comparative Example 7 | P-D5 | C-1X | H-B | E-1 | +701 | +110 |
| Comparative Example 8 | P-D6 | C-2Y | H-B | E-1 | +700 | +108 |

The photosensitive layers of the multi-layer type photosensitive members (P-A1) to (P-A6) and the single-layer type photosensitive members (P-C1) to (P-C8) included, as the hole transport material, the compound (1), more specifically, any of the compounds (H-1) to (H-8). Thus, the photosensitive members had a smaller absolute value of the sensitivity potential ($V_L$) and excellent electric characteristics, as is clear from Tables 2 and 3.

On the other hand, the photosensitive layers of the multi-layer type photosensitive members (P-B1) and (P-B2) and the single-layer type photosensitive members (P-D1) to (P-D6) did not contain the compound (1) as hole transport materials. Thus, as is clear from Tables 2 and 3, the photosensitive members have a larger absolute value of the sensitivity potential ($V_L$) and poor electric characteristics.

<Production of Multi-Layer Type Photosensitive Members (P-E1) to (P-E12)>

The multi-layer type photosensitive members (P-E1) to (P-E12) were produced using materials for forming the photosensitive layers described above.

(Production of Multi-Layer Type Photosensitive Member (P-E1))

First, a titanium oxide ("Sample SMT-A" produced by TAYCA Corporation with a number average primary particle size of 10 nm) subjected to surface treatment was prepared. More specifically, the titanium oxide was subjected to surface treatment using alumina and silica, and the surface-treated titanium oxide was further subjected to surface treatment using methyl hydrogen polysiloxane while subjecting the titanium oxide to wet dispersion to prepare a substance resulting therefrom.

Next, an application liquid for an undercoat layer was prepared. More specifically, 2 parts by mass of the surface-treated titanium oxide, 1 part by mass of a polyamide resin ("Amilan (registered Japanese trademark) CM8000" produced by Toray Industries, Inc., a quaternary copolymer with nylon 6, nylon 12, nylon 66, and nylon 610), 10 parts by mass of methanol as a solvent, 1 part by mass of butanol as a solvent, and 1 part by mass of toluene as a solvent were introduced into a container. Contents of the container were mixed with a bead mill for five hours, and the material were dispersed in the solvent. Consequently, an application liquid for an undercoat layer was obtained.

Next, an undercoat layer was formed. More specifically, the obtained application liquid for an undercoat layer was filtered with a 5 m-sized filter. Then the application liquid for an undercoat layer was applied to a surface of a drum-shaped support body (with a diameter of 30 mm and a full length of 246 mm) of aluminum as a conductive substrate by using dip coating. Subsequently, the applied application liquid for an undercoat layer was heated at 130° C. for thirty minutes. Consequently, an undercoat layer (with a film thickness of 2 μm) was formed on the conductive substrate.

Next, an application liquid for charge generating layer formation was prepared. More specifically, 1.5 parts by mass of a compound (C-2Y) as a charge generating material, 1 part by mass of a polyvinyl acetal resin ("S-LEC BX-5" produced by SEKISUI CHEMICAL CO. LTD.) as a base resin, 40 parts by mass of propylene glycol monomethyl ether as a dispersion medium, and 40 parts by mass of tetrahydrofuran as dispersion medium were introduced into a container. Contents of the container were mixed with a bead mill for two hours, and the materials were dispersed in the dispersion medium. Consequently, an application liquid for charge generating layer formation was obtained. Next, the obtained application liquid for charge generating layer formation was filtered with a 3 m-sized filter. Then the application liquid for charge generating layer formation was applied to the formed undercoat layer by dip coating. Subsequently, the applied application liquid for charge generating layer formation was dried at 50° C. for five minutes. Consequently, a charge generating layer (with a film thickness of 0.3 μm) was formed on the undercoat layer.

Next, an application liquid for charge transport layer formation was prepared. More specifically, 50 parts by mass of the compound (H-1) as a hole transport material, 100 parts by mass of the resin (Resin-1a) as a binder resin, 2 parts by mass of a hindered phenol-based antioxidant ("IRGANOX (registered Japanese trademark) 1010" produced by BASF) as an additive, 5 parts by mass of silica particles ("Aerosil (registered Japanese trademark) RX200" produced by Nippon Aerosil Co., Ltd, with a number average primary particle size of 12 nm) surface-treated with hexamethyldisilazane as an additive, 560 parts by mass of tetrahydrofuran as a solvent, and 140 parts by mass of toluene as a solvent were introduced into a container. A ratio of the mass of the tetrahydrofuran relative to the mass of toluene (tetrahydrofuran/toluene) was 8/2 (that is, 4). Contents of the container were mixed with a cyclic ultrasonic disperser for 12 hours. Consequently, the materials were dispersed in the solvent. As a result, an application liquid for charge transport layer formation was obtained. Next, the obtained application liquid for charge transport layer formation was applied onto the formed charge generating layer by the same method as that used for the application liquid for charge generating layer formation. Subsequently, the applied application liquid for charge transport layer formation was dried at 120° C. for 40 minutes. Consequently, a charge transport layer (with a film thickness of 30 μm) was formed on the charge generating layer. As a result, the multi-layer type photosensitive member (P-E1) was obtained.

(Production of Multi-Layer Type Photosensitive Member (P-E2) to (P-E12))

The multi-layer type photosensitive members (P-E2) to (P-E12) were each produced by the same method as that used for producing the multi-layer type photosensitive member (P-E1) with only the following points changed. A type of the hole transport material were changed from the compound (H-1) used for producing the multi-layer type photosensitive member (P-E1) to a hole transport material of the type illustrated in Table 4. A type of the binder resin was altered from the resin (Resin-1a) used for producing the multi-layer type photosensitive member (P-E1) to a resin of the type illustrated in Table 4.

(Evaluation of Electrical Characteristics of Multi-Layer Type Photosensitive Members (P-E1) to (P-E12))

The electric characteristics of each of the produced multi-layer type photosensitive members (P-E1) to (P-E12) were evaluated. The evaluation of the electric characteristics was performed under environment with a temperature of 23° C. and a humidity of 50% RH (relative humidity). First, a surface of the multi-layer type photosensitive member was charged at −800V using a drum sensitivity test device (produced by GEN-TECH INC.). Next, monochromatic light (with a wavelength of 780 nm, a half-width of 20 nm, and a light quantity of 1.0 μJ/cm$^2$) was extracted from white light of a halogen lamp by using a bandpass filter. The extracted monochromatic light was irradiated (exposed) to a surface of the multi-layer type photosensitive member. A surface potential of the multi-layer type photosensitive member upon passage of 50 milliseconds after ending of the irradiation was measured. The measured surface potential was provided as sensitivity potential ($V_L$, unit of V) Table 4 illustrates the measured sensitivity potential ($V_L$) of the multi-layer type photosensitive member. Table 4 indicates that with a smaller absolute value of the sensitivity potential, the electric characteristics of the multi-layer type photosensitive member is more favorable.

(Evaluation of Abrasion Resistance of Multi-Layer Type Photosensitive Members (P-E1) to (P-E12))

The abrasion resistance of each of the produced multi-layer type photosensitive members (P-E1) to (P-E12) was evaluated. More specifically, the application liquid for charge transport layer formation used for producing each multi-layer type photosensitive member was applied to a polypropylene sheet (with a thickness of 0.3 mm) wound around an aluminum pipe (with a diameter of 78 mm). The application liquid for charge transport layer formation applied to the polypropylene sheet was dried at 120° C. for 40 minutes. Consequently, an evaluation sheet (with a thickness of 30 μm) was formed on the polypropylene sheet. Subsequently, the evaluation sheet was removed from the polypropylene sheet. Then the removed evaluation sheet was attached to a specimen mounting card ("S-36" produced by TABAR Industries) to obtain a test piece.

Next, mass MA of the test piece before an abrasion test was measured. Then the abrasion test was performed on the test piece. More specifically, the test piece was fitted on a rotary base of a rotary ablation tester (produced by TOYO SEIKI SEISAKU-SHO, LTD). Then an abrasion wheel ("CS-10" produced by TABER Industries) having a load of 500 gf loaded on the test piece, the rotary base was rotated at a rotational speed of 60 rpm and an abrasion test with 1000 rotations was performed. Subsequently, mass MB of the test piece after the abrasion test was measured. Then a decrease of abrasion (=MA-MB), i.e., an amount of a mass change of the test piece across the abrasion test was obtained. Table 4 illustrates that the obtained decrease of abrasion. Table 4 indicates that with a smaller decrease of abrasion, the abrasion resistance of the multi-layer type photosensitive member is more favorable.

TABLE 4

| Multi-layer type photosensitive member | Charge transport layer Hole transport material | Binder resin | Electric characteristics $V_L$ (V) | Abrasion resistance Decrease of abrasion (mg) |
|---|---|---|---|---|
| Example 1 | P-E1 | H-1 | Resin-1a | −60 | 5.5 |
| Example 2 | P-E2 | H-2 | Resin-1a | −61 | 6.1 |
| Example 3 | P-E3 | H-3 | Resin-1a | −70 | 5.3 |
| Example 4 | P-E4 | H-4 | Resin-1a | −63 | 6.3 |
| Example 5 | P-E5 | H-5 | Resin-1a | −72 | 5.9 |
| Example 6 | P-E6 | H-6 | Resin-1a | −72 | 5.9 |
| Example 7 | P-E7 | H-1 | Resin-2a | −67 | 6.2 |
| Example 8 | P-E8 | H-1 | Resin-3a | −63 | 7.0 |
| Example 9 | P-E9 | H-1 | Resin-4a | −61 | 5.0 |
| Example 10 | P-E11 | H-1 | Resin-5a | −76 | 9.5 |
| Comparative Example 1 | P-E10 | H-A | Resin-1a | −95 | 8.6 |
| Comparative Example 2 | P-E12 | H-B | Resin-1a | −85 | 8.8 |

The photosensitive layers of the multi-layer type photosensitive members (P-E1) to (P-E9) and (P-E11) contained the compound (1) as a hole transport material. More specifically, the aforementioned photosensitive layers contained the compounds (H-1) to (H-6) as hole transport materials. Thus, as is clear from Table 4, the aforementioned multi-layer type photosensitive members have small absolute values of sensitivity potential ($V_L$) and excellent electric characteristics.

The photosensitive layers of the multi-layer type photosensitive members (P-E1) to (P-E9) included: a charge generating layer containing a charge generating material; and a charge transport layer containing a hole transport material and a binder resin. The compound (1) was contained as the hole transport material. More specifically, the compound (H-1) to (H-6) were contained as hole transport materials. The resin (2) was contained as the binder resin. More specifically, the resins (Resin-1a) to (Resin-4a) were contained as the binder resins. Thus, as is clear from Table 4, the aforementioned multi-layer type photosensitive members have small absolute values of sensitivity potential ($V_L$) and particularly excellent electric characteristics. The multi-layer type photosensitive members had a small decrease of abrasion and excellent abrasion resistance.

The photosensitive layers of the multi-layer type photosensitive members (P-E10) and (P-E12) contained either of the compounds (H-A) and (H-B) as a hole transport material. However, the compounds (H-A) and (H-B) were not compounds represented by the general formula (1). Thus, as is clear from Table 4, the multi-layer type photosensitive members (P-E10) and (P-E12) had large absolute values of sensitivity potential ($V_L$) and poor electric characteristics. The multi-layer type photosensitive members had a large decrease of abrasion and poor abrasion resistance.

The above proves that the compound (1) improves the electric characteristics of the photosensitive member when contained in the photosensitive layer. The photosensitive member including a photosensitive layer containing the compound (1) exhibited excellent electric characteristics. Further, the photosensitive member produced by the production method of the present disclosure exhibited excellent electric characteristics.

What is claimed is:

1. A triarylamine derivative represented by general formula (1) below:

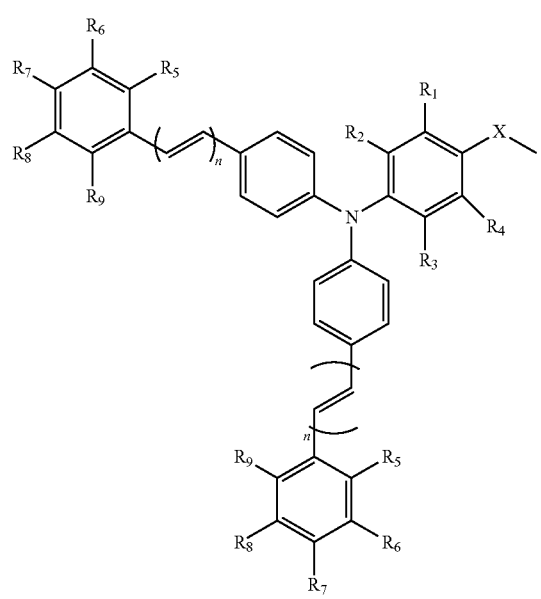

(1)

-continued

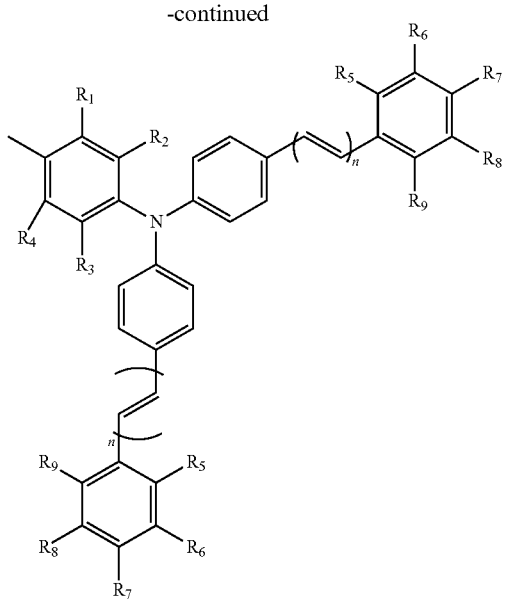

wherein in the general formula (1), $R_1$, $R_4$, $R_5$, $R_6$, $R_7$, $R_8$, and $R_9$ each represent a hydrogen atom, $R_2$ represents an alkyl group having a carbon number of at least 1 and no greater than 4, $R_3$ represents an alkyl group having a carbon number of at least 1 and no greater than 4, the alkyl group being different from the alkyl group represented by $R_2$, X represents an alkylene group having a carbon number of at least 1 and no greater than 6 or an oxygen atom, and n represents 2.

2. The triarylamine derivative according to claim 1, wherein in the general formula (1), $R_1$, $R_4$, $R_5$, $R_6$, $R_7$, $R_8$ and $R_9$ each represent a hydrogen atom, $R_2$ represents an alkyl group having a carbon number of at least 1 and no greater than 4, $R_3$ represents an alkyl group having a carbon number of at least 1 and no greater than 4, the alkyl group being different from the alkyl group represented by $R_2$, X represents an alkylene group having a carbon number of at least 1 and no greater than 3, and n represents 2.

3. An electrophotographic photosensitive member comprising a conductive substrate; and a photosensitive layer containing a charge generating material and a hole transport material, wherein the hole transport material is a triarylamine derivative represented by chemical formula (H-1), (H-3), or (H-5)

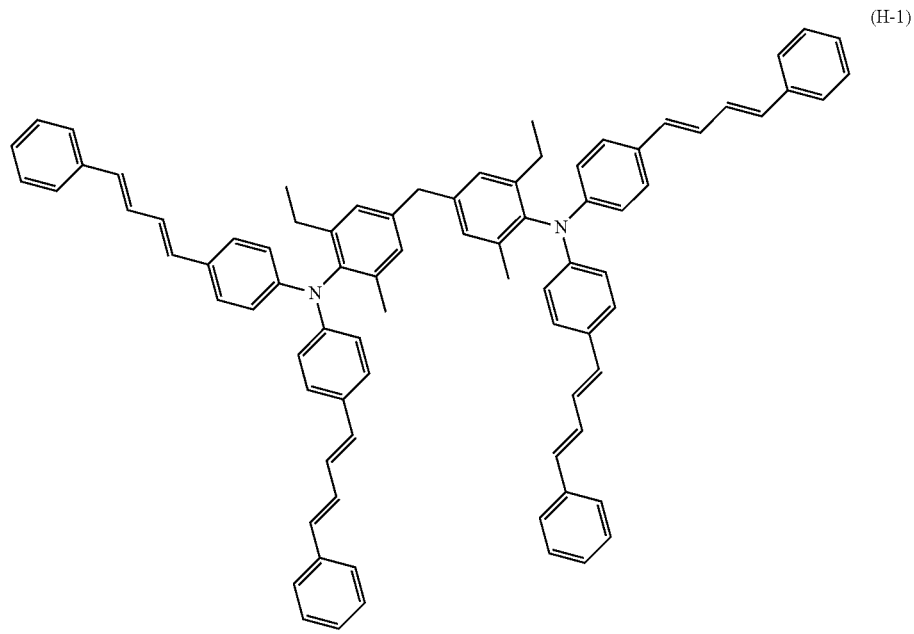 [SMILES: CCc1cc(Cc2cc(C)c(N(c3ccc(/C=C/C=C/c4ccccc4)cc3)c3ccc(/C=C/C=C/c4ccccc4)cc3)c(CC)c2)cc(C)c1N(c1ccc(/C=C/C=C/c2ccccc2)cc1)c1ccc(/C=C/C=C/c2ccccc2)cc1]
(H-1)
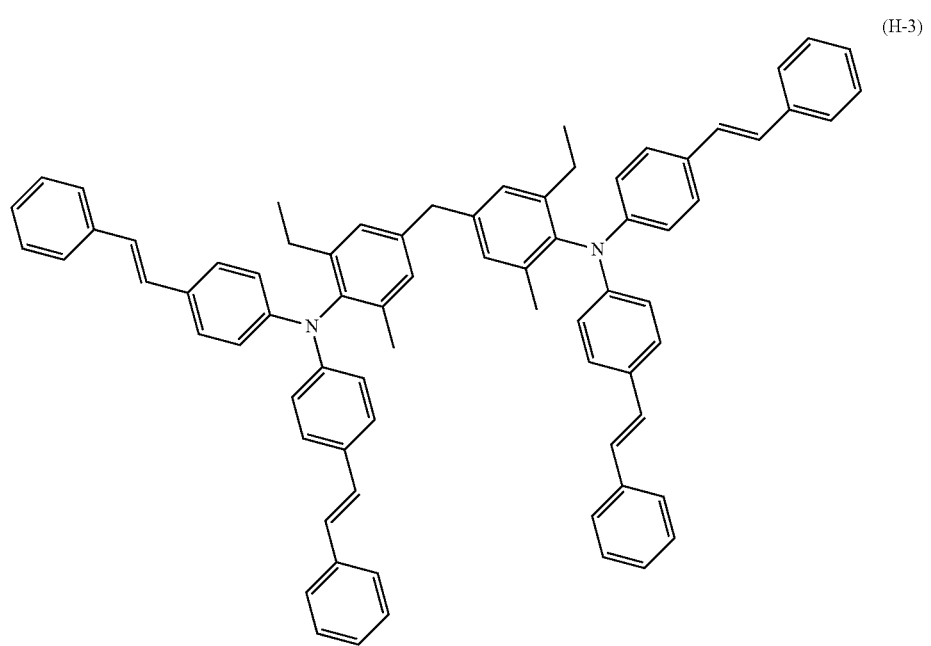 [SMILES: CCc1cc(Cc2cc(C)c(N(c3ccc(/C=C/c4ccccc4)cc3)c3ccc(/C=C/c4ccccc4)cc3)c(CC)c2)cc(C)c1N(c1ccc(/C=C/c2ccccc2)cc1)c1ccc(/C=C/c2ccccc2)cc1]
(H-3)

-continued

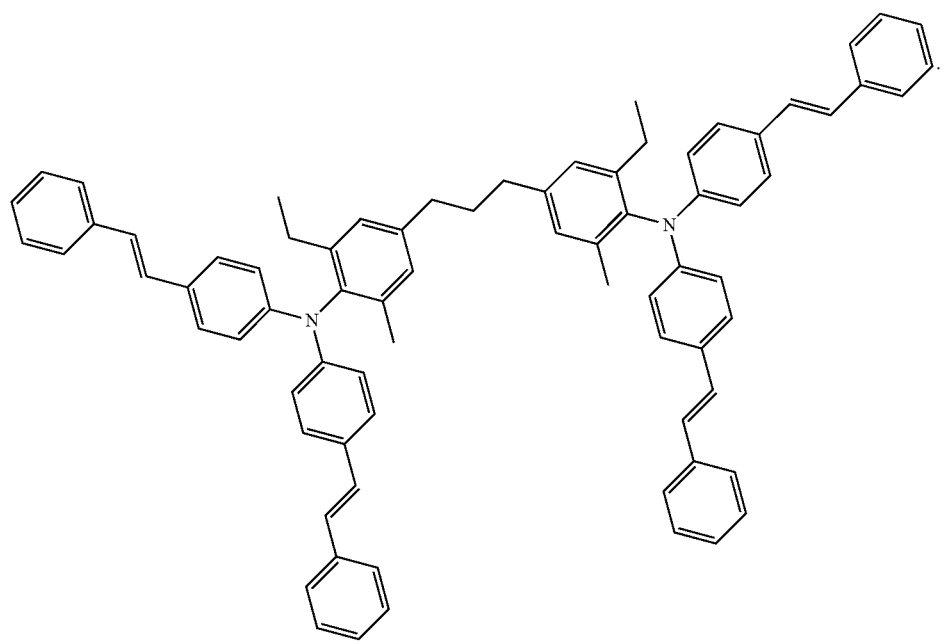

(H-5)

4. The electrophotographic photosensitive member according to claim 3, wherein
a charge generating layer containing the charge generating material and a charge transport layer containing the hole transport material are included as the photosensitive layer, or a single-layer type photosensitive layer containing the charge generating material and the hole transport material is included as the photosensitive layer.

5. The electrophotographic photosensitive member according to claim 3, wherein
the photosensitive layer includes: a charge generating layer containing the charge generating material; and a charge transport layer containing the hole transport material and a binder resin, and
the binder resin is a polycarbonate resin having a repeating unit represented by general formula (2) below:

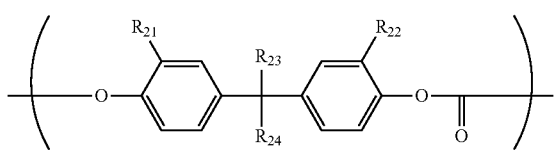

(2)

where
$R_{21}$ and $R_{22}$ each represent, independently from each other, a hydrogen atom, an alkyl group, or an aryl group, and
$R_{23}$ and $R_{24}$ each represent, independently from each other, a hydrogen atom, an alkyl group, or an aryl group, or $R_{23}$ and $R_{24}$ bond to each other to represent a cycloalkylidene group.

6. The electrophotographic photosensitive member according to claim 5, wherein
in the general formula (2),
$R_{21}$ and $R_{22}$ each represent, independently from each other, a hydrogen atom or an alkyl group having a carbon number of at least 1 and no greater than 4, and
$R_{23}$ and $R_{24}$ each represent, independently from each other, a hydrogen atom or an alkyl group having a carbon number of at least 1 and no greater than 4, or $R_{23}$ and $R_{24}$ bond to each other to represent a cycloalkylidene group having a carbon number of at least 5 and no greater than 7.

7. The electrophotographic photosensitive member according to claim 5, wherein
in the general formula (2),
$R_{21}$ and $R_{22}$ each represent, independently from each other, a hydrogen atom or an alkyl group having a carbon number of at least 1 and no greater than 4, and
$R_{23}$ and $R_{24}$ each represent, independently from each other, an alkyl group having a carbon number of at least 1 and no greater than 4, or $R_{23}$ and $R_{24}$ bond to each other to represent a cycloalkylidene group having a carbon number of at least 5 and no greater than 7.

8. The electrophotographic photosensitive member according to claim 3, wherein
the photosensitive layer is a single-layer type photosensitive layer containing the charge generating material, the hole transport material, and an electron transport material, and
the electron transport material is a compound represented by general formula (8) below:

(8)

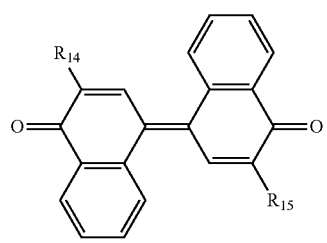

where
R$_{14}$ and R$_{15}$ each represent, independently from each other, a hydrogen atom, a cyano group, an optionally substituted alkyl group, an optionally substituted alkenyl group, an optionally substituted alkoxy group, an optionally substituted alkoxycarbonyl group, an optionally substituted aryl group, or an optionally substituted heterocyclic group.

9. The electrophotographic photosensitive member according to claim 3, wherein
the charge generating material is titanyl phthalocyanine having a y-form crystal structure.

10. The electrophotographic photosensitive member according to claim 5, wherein
the polycarbonate resin having a repeating unit represented by the general formula (2) is a resin having a repeating unit represented by chemical formula (Resin-1) or (Resin-4) below:

(Resin-1)

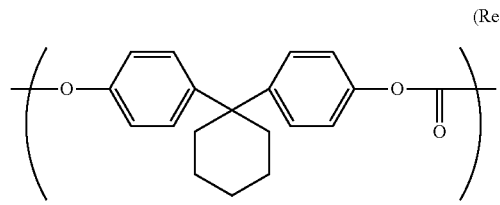

(Resin-4)

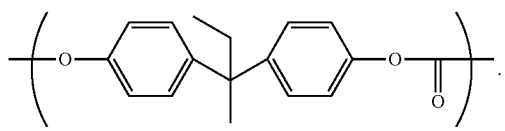

11. The electrophotographic photosensitive member according to claim 5, wherein
the charge transport layer further contains silica particles surface-treated with hexamethyldisilazane,
the triarylamine derivative is represented by the chemical formula (H-1), (H-3), or (H-5), and
the polycarbonate resin having a repeating unit represented by the general formula (2) is a resin having a repeating unit represented by chemical formula (Resin-1) or (Resin-4) below:

(Resin-1)

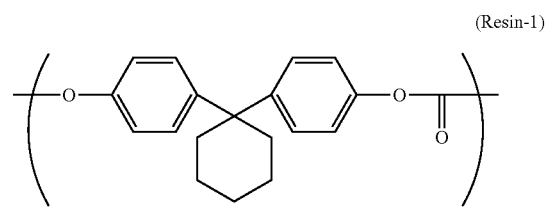

(Resin-4)

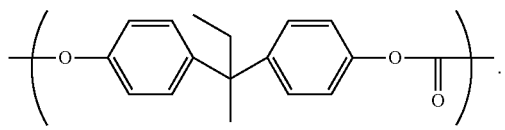

* * * * *